United States Patent [19]
McWhorter et al.

[11] Patent Number: 5,773,610
[45] Date of Patent: Jun. 30, 1998

[54] OPTICALLY ACTIVE 3-(1-(ALKYLAMINO)) ALKYL PYRROLIDINES

[75] Inventors: William W. McWhorter, Parchment; Thomas J. Fleck, Scotts; Bruce A. Pearlman, Kalamazoo, all of Mich.

[73] Assignee: Pharmacia & Upjohn Company, Kalamazoo, Mich.

[21] Appl. No.: 549,793

[22] PCT Filed: May 3, 1994

[86] PCT No.: PCT/US94/04548

§ 371 Date: Nov. 1, 1995

§ 102(e) Date: Nov. 1, 1995

[87] PCT Pub. No.: WO94/26708

PCT Pub. Date: Nov. 24, 1994

Related U.S. Application Data

[63] Continuation-in-part of Ser. No. 58,611, May 6, 1993, abandoned.

[51] Int. Cl.$^6$ .................................................. C07D 205/08
[52] U.S. Cl. .......................................... 540/200; 540/362
[58] Field of Search ..................................... 540/200, 362

[56] References Cited

U.S. PATENT DOCUMENTS 5,157,128  10/1992  Hagen et al. ........................ 548/566

FOREIGN PATENT DOCUMENTS

| 0443498A1 | 8/1991 | European Pat. Off. . |
| 72476 | 3/1991 | Japan . |
| 92-09596 | 6/1992 | WIPO . |

OTHER PUBLICATIONS

Guanti, Giuseppe, et al, in *Tetrahedron Letters* 28 (37), pp. 4335–4338 (1987).
Seebach and Esterman, *Tetrahedron Letters*, 28, 27, pp. 3103–3106 (1987).
Database WPI Week 9119, Derwent Publication Ltd. aN 91–136059 and JP A 3 072 476, 1991.
Hagen, Susan E., et al., *Journ. of Medicinal Chem.*, 37, 6, pp. 733–738 (1994).
Domagala, John M., et al., *Journ. of Medicinal Chem.*, 36, 7, pp. 871–882 (1993).
Plummer, Janet S., et al., *Tetrahedron Letters*, 34, 47, pp. 7529–7532 (1993).
Archelas, A., et al., *Tetrahedron Letters*, 29, 50, pp. 6611–6614 (1988).
Liebeskind, Lanny S., et al., *Journ of the American Chem. Soc.*, 108, 29, pp. 6328–6343 (1986).
M. C. Schroeder, et al., Journal of Heterocyclic Chemistry, vol. 29, No. 6, pp. 1481–1498 (1992).
V. Estermann, et al., Helvetica Chimica Acta, vol. 71, pp. 1824–1839 (1988).
M. Furukawa et al., Chemical Pharmaceutical Bulletin, vol. 27(9), pp. 2223–2226 at 6 (1979).
Helvetica Chimica Acta, vol. 66, Fasc. 2, Nr. 38, p. 461 (1983).
S. Davies, et al., Tetrahedron: Asymmetry, vol. 2, No. 3, pp. 183–186 (1991).
S. Davies, "Chiral Lithium Organoamide Technology Available," from Oxford Asymmetry Limited, Oxfordshire, UK., 1991.
F. Orsini, et al., Synthetic Communications, vol. 12, No. 14, pp. 1147–1154 (1982).
F. A. Davis, etal., Journal of the American Chemical Society, vol. 109, No. 11, pp. 3370–3377 (1987).

*Primary Examiner*—Joseph McKane
*Attorney, Agent, or Firm*—Thomas A. Wootton

[57] ABSTRACT

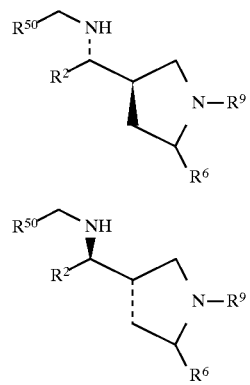

This invention relates to processes for the synthesis of various optically active amino pyrrolidinyl stereoisomers, or enantiomers, that may be attached to quinolonecarboxylic acids or naphthyridones. Processes and essential intermediates are disclosed and claimed for the synthesis of compounds represented by the structure shown in FIG. BG$_{4-1}$, where R$^{50}$, R$^6$ and R$^9$ are defined independently and are H, -(C$_1$–C$_8$)alkyl, -(C$_3$–C$_8$)cycloalkyl, -(C$_1$–C$_8$)alkyl-(C$_3$–C$_8$) cycloalkyl, -(C$_6$–C$_{12}$ aryl), -(C$_1$–C$_8$)alkyl-(C$_6$–C$_{12}$ aryl), or the aryl or alkyl is substituted with one to three of the following groups, (C$_6$–C$_{12}$ aryl), (C$_1$–C$_3$)alkyl, (C$_1$–C$_3$) alkoxy, halogen, trifluoromethyl; where R$^2$ is -(C$_1$–C$_8$)alkyl, -(C$_3$–C$_8$)cycloalkyl, -(C$_1$–C$_8$)alkyl-(C$_3$–C$_8$)cycloalkyl, -(C$_6$–C$_{12}$ aryl), -(C$_1$–C$_8$)alkyl-(C$_6$–C$_{12}$ aryl), or the aryl or alkyl is substituted with one to three of the following groups, -(C$_6$–C$_{12}$ aryl), -(C$_1$–C$_3$)alkyl,-(C$_1$–C$_3$)alkoxy, halogen, trifluoromethyl; depending upon the starting materials used, compounds represented by the structure shown by FIG. BG$_{4-1}$ may have one of either of the two stereochemical arrangements shown, or, if the starting materials are a racemic mixture, the reaction may produce a 1:1 ratio of the combination of products shown in FIG. BG$_{4-1}$, i.e. a racemic mixture.

6 Claims, No Drawings

OPTICALLY ACTIVE 3-(1-(ALKYLAMINO)) ALKYL PYRROLIDINES

This application is a 371 application of International Application No. PCT/US94/04548, International Filing Date, 3 May 1994, which was a continuation-in-part application of U.S. patent application Ser. No. 08/058,611, filed 6 May 1993, now abandoned.

FIELD OF THE INVENTION

This method allows the convenient, large scale preparation for compounds, possibly used as intermediates of quinolones, in high optical purity and good yield. Previously published methods lack adequate stereoselectivity for large scale preparation or are impractical for large scale preparation.

BACKGROUND OF THE INVENTION

The quinolonecarboxylic acid based antibacterial agents such as norfloxacin and ciprofloxacin, now used clinically, exhibit potent antibacterial activity. Efforts to synthesize or discover a quinolone based antibacterial compound exhibiting maximum antibacterial properties and minimum toxic side effects continue. Many investigators have focused their efforts on developing quinolones with aminoalkyl pyrrolidinyl moieties attached to the 7 position of the quinolone.

Within the chiral environment of living organisms, individual stereoisomers of biologically active compounds are often known to have unique properties relative to their related stereoisomers. In vitro and in vivo studies of quinolone derivatives with various aminoalkyl pyrrolidinyl 7 position side chains have shown that the activity of these compounds can be strongly influenced by the stereochemical positions of the atoms in the side chain. European Patent Application - Publication 0,443,498 A1, published 28 Aug. 1991, discloses an aminoalkyl pyrrolidinyl 7 position side chain quinolones having 2 asymmetric carbon atoms on a 3-amino-4-methylpyrrolidine ring attached to the 7 position of a quinolone. Two of the four possible stereochemical isomers were two to six times more active than the other two stereoisomers. U.S. Pat. No. 5,157,128, issued 20 Oct. 1992, (Hagen) describes the effect of stereospecific alkylation at the 1'-aminoethyl position of a 3-pyrrolidine substituent also substituted at the 7 position of a quinolone. Hagen reported that the R-(1,1-dialkylated-1-aminomethyl)pyrrolidine, when coupled at the 7 position of a quinolone leads to antibacterial agents with improved activity and safety.

This invention relates to a process for the synthesis of various optically active amino pyrrolidinyl stereoisomers, or enantiomers, that may be attached to quinolonecarboxylic acids or naphthyridones. The process disclosed by the procedures and examples herein allow the synthesis of these side chains in a more efficient manner than any previously disclosed method of synthesis. Novel intermediates are also disclosed.

INFORMATION DISCLOSURE

Kokai Patent Application No. Hei 3 (1991)-72476, discloses the preparation of similar compounds using a less selective method of synthesis. Another less selective method of synthesis is provided in the Journal of Heterocyclic Chemistry, Vol. 29, No. 6, pp. 1481–98 (1992), also mentioned below. U.S. Pat. No. 5,157,128 issued 20 Oct., 1992, (Hagen), discloses optically pure isomers of 7-(3-(1,1-dialkylmethyl-1-amino)-1-pyrrolidinyl quinolones and naphthyridones and their method of manufacture. Guanti, Giuseppe, et al. in Tetrahedron Letter, Vol. 28, No. 37, pp. 4335–4338 (1987) discuss a stereocontrolled synthesis of 3-(1'-hydroxyethyl)-2-azetidinones through trimethylsilyl trifluoromethanesulphonate catalyzed condensation of silyl ketene acetal. Estermann and Seebach, Helvetica Chimica Acta, Vol. 71 pp. 1824–39 (1988) discloses diastereoselective alkylation of N-protected 3-aminobutanoic acid esters at the 2 position. Seebach and Esterman, Tetrahedron Letters, Vol.28, No. 27 pp. 3310–3106 (1987) add additional discussion concerning alkylation of benzaldehyde to give enantiomerically pure 3-aminobutanoic acid derivatives. Furukawa et. al., Chemical Pharmaceutical Bulletin, Vol. 27. pp. 2223–6 at 6 (1979) discloses the use of Pearlman's reagent, 10% palladium hydroxide on charcoal, to hydrogenolytically remove benzyl groups from amines. The protection of the amino group with protecting groups such as carboxy benzyl are disclosed in Helvetica Chimica Acta, Vol. 66, Fasc. 2, Nr. 38, p. 461 (1983). Davies, in both Tetrahedron:Asymmetry, Vol. 2, No. 3, pp. 183–186 (1991) and in commercial literature, see, "Chiral Lithium Organoamide Technology Available," from Oxford Asymmetry Limited, Oxfordshire, UK. (Lithium Link), discloses the use of lithium organoamides in stereoselective Michael additions to crotonate esters. Orsini et. al., Synthetic Communications, Vol. 12, No. 14, pp. 1147–54 (1982) and Davis et. al., Journal of the American Chemical Society, Vol. 109, No. 11, pp. 3370–7 (1987) provide examples of the preparation of the starting materials used in this method. The reduction of anmides and urethanes to amines using lithium aluminium hydride is well known and there are many examples of this transformation in the chemical literature: for an example, see Journal of Heterocyclic Chemistry, Vol. 29, No. 6, pp. 1481–98 (1992). All the references provided above incorporated by reference into this document.

SUMMARY OF THE INVENTION

This invention relates to processes for the synthesis of various optically active amino pyrrolidinyl stereoisomers, or enantiomers, that may be attached to quinolonecarboxylic acids or naphthyridones or other appropriate compounds. Processes and essential intermediates are disclosed for the synthesis of compounds represented by the structure shown in FIG. $BG_5$, below.

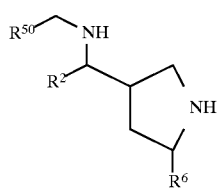

FIG. $BG_5$ where $R^{50}$ is is H, -($C_1$–$C_8$)alkyl, -($C_3$–$C_8$)cycloalkyl, -($C_1$–$C_8$)alkyl-($C_3$–$C_8$)cycloalky, -($C_6$–$C_{12}$ aryl), -($C_1$–$C_8$) alkyl-($C_6$–$C_{12}$ aryl), or the aryl or alkyl is substituted with one to three of the following groups, ($C_6$–$C_{12}$ aryl),($C_1$–$C_3$) alkyl, ($C_1$–$C_3$) alkoxy, halogen, trifluoromethyl, where $R^2$ is -($C_1$–$C_8$)alkyl, -($C_3$–$C_8$)cycloalkyl, -($C_1$–$C_8$) alkyl-($C_3$–$C_8$)cycloalkyl, -($C_6$–$C_{12}$ aryl), -($C_1$–$C_8$)alkyl-($C_6$–$C_{12}$ aryl), or the aryl or alkyl is substituted with one to three of the following groups, ($C_6$–$C_{12}$ aryl),($C_1$–$C_3$)alkyl, ($C_1$–$C_3$) alkoxy, halogen, trifluoromethyl;

where $R^6$ is H, -($C_1$–$C_8$)alkyl, -($C_3$–$C_8$)cycloalkyl, -($C_1$–$C_8$) alkyl-($C_3$–$C_8$)cycloalkyl, -($C_6$–$C_{12}$ aryl), -($C_1$–$C_8$)alkyl- ($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl;

Depending upon the starting materials used, compounds represented by the structure shown by FIG. BG$_5$ may have one of either of the two steriochemical arrangements shown by the structures below, FIG. BG$_{5-1}$,

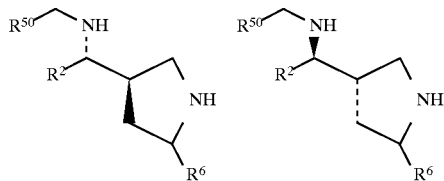

FIG. BG$_{5-1}$ or, if the starting materials are a racemic mixture, the reaction may produce a 1:1 ratio of the combination of products shown in FIG. BG$_{5-1}$, i.e. a racemic mixture.

This invention discloses two separate and distinct but related procedures for preparing the various enantiomers. Both procedures are significant advances in the art. The first group of procedures are described under the various reactions labeled as CHART A and CHART B reactions. The second major group of reactions are described under the various reactions labeled as CHART C, CHART D, CHART E and CHART F reactions.

The reactions from CHART A and CHART B are summarized below. This part of the invention comprises a series of reactions beginning with subjecting a compound or compounds represented by the structure shown in FIG. AG$_0$, below,

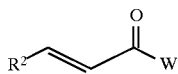

FIG. AG$_0$ and W is C$_1$, Br, —SR$^2$ or FIG. to right,

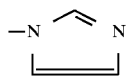

to treatment with R$^3$XLi
where R$^3$ is -(C$_1$–C$_8$)alkyl, -(C$_3$–C$_8$)cycloalkyl, -(C$_1$–C$_8$) alkyl-(C$_3$–C$_8$)cycloalkyl, -(C$_6$–C$_{12}$aryl), -(C$_1$–C$_8$)alkyl-(C$_6$–C$_{12}$ aryl), or the aryl or alkyl is substituted with one to three of the following groups, -(C$_6$–C$_{12}$ aryl), -(C$_1$–C$_3$)alkyl, -(C$_1$–C$_3$) alkoxy, halogen, trifluoromethyl, and where X is O, NH, S, to obtain a compound represented by the structure shown in FIG. AG$_{1(a)}$, below

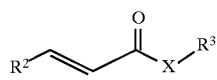

FIG. AG$_{1(a)}$ which is then reacted with a compound represented by the deprotonated form of the structure formed in FIG. AG$_{1(b)}$, below, or its appropriate isomer,

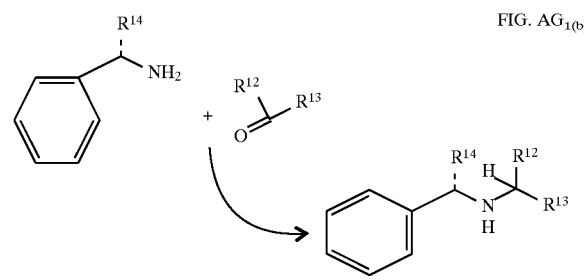

FIG. AG$_{1(b)}$ where R$^{12}$ is (C$_6$–C$_{12}$ aryl), or the aryl is substituted with one to three of the following groups, (C$_1$–C$_3$)alkyl, (C$_1$–C$_3$) alkoxy, halogen, trifluoromethyl;

R$^{13}$ is H, -(C$_1$–C$_8$)alkyl, -(C$_3$–C$_8$)cycloalkyl, -(C$_1$–C$_8$)alkyl-(C$_3$–C$_8$)cycloalkyl, -(C$_6$–C$_{12}$ aryl), -(C$_1$–C$_8$)alkyl-(C$_6$–C$_{12}$ aryl), or the aryl or alkyl is substituted with one to three of the following groups, -(C$_6$–C$_{12}$ aryl), -(C$_1$–C$_3$)alkyl, -(C$_1$–C$_3$) alkoxy, halogen, trifluoromethyl,
where R$^{14}$ is -(C$_1$–C$_8$)alkyl, -(C$_3$–C$_8$)cycloalkyl, -(C$_1$–C$_8$) alkyl-(C$_3$–C$_8$)cycloalkyl, -(C$_6$–C$_{12}$ aryl), -(C$_1$–C$_8$)alkyl-(C$_6$–C$_{12}$ aryl), or the aryl or alkyl is substituted with one to three of the following groups, -(C$_6$–C$_{12}$ aryl), -(C$_1$–C$_3$)alkyl, -(C$_1$–C$_3$) alkoxy, halogen, trifluoromethyl;
to produce the compounds represented by the structures shown in FIG. AG$_2$, below,

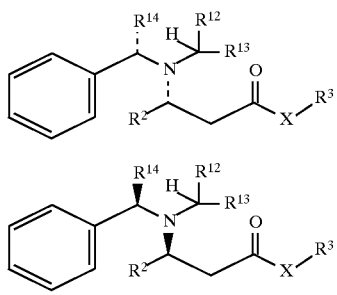

FIG. AG$_2$ the compounds of FIG. AG$_2$ are then deprotected under hydrogenolysis conditions with a reducing agent such as Pearlman's catalyst, 10 percent palladium hydroxide on charcoal, to obtain the compounds, represented by the structures shown in FIG. AG$_3$, below,

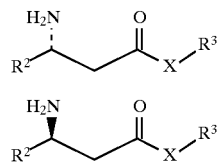

FIG. AG$_3$ the compounds represented by the structure shown in FIG. AG$_3$ are then used according to the procedures described the reactions of CHART B to produce the desired compounds.

The reactions of CHART B comprises, using starting materials represented by the structure shown in FIG. BG$_{0-1}$, which are the same compounds represented by FIG. AG$_3$, below,

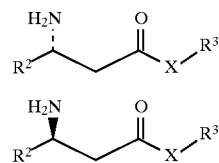

FIG. BG$_{0-1}$ where R$^2$ and R$_3$ is -(C$_1$–C$_8$)alkyl, -(C$_3$–C$_8$)cycloalkyl, -(C$_1$–C$_8$)alkyl-(C$_3$-C$_8$)cycloalkyl, -(C$_6$–C$_{12}$ aryl), -(C$_1$–C$_8$) alkyl-(C$_6$–C$_{12}$ aryl), or the aryl or alkyl is substituted with one to three of the following groups, (C$_6$–C$_{12}$ aryl),(C$_1$–C$_3$) alkyl, (C$_1$–C$_3$) alkoxy, halogen, trifluoromethyl;
X is O, NH, S reacting those starting materials with a compound represented by the structure in FIG. BG-R$_1$, below,

FIG. BG-R1 where R$^1$ is H, -(C$_1$–C$_8$)alkyl, -(C$_3$–C$_8$)cycloalkyl, -(C$_1$–C$_8$) alkyl-(C$_3$–C$_8$)cycloalkyl, -(C$_6$–C$_{12}$aryl), -(C$_1$–C$_8$)alkyl- ($C_6$–$C_{12}$ aryl), —O—($C_{1-8}$ alkyl), —O—($C_{3-8}$ cycloalkyl), —O—($C_{1-8}$ alkyl)($C_{3-8}$ cycloalkyl), —O—($C_{6-12}$ aryl), —O—($C_{1-8}$ alkyl)-aryl, or the aryl or alkyl is substituted with one to three of the following groups, ($C_6$–$C_{12}$ aryl), ($C_1$–$C_3$)alkyl, ($C_1$–$C_3$) alkoxy, halogen, trifluoromethyl, Z is Cl, $N_3$, S- ($C_6$–$C_{12}$)aryl,

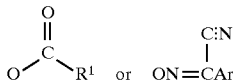

in a suitable organic solvent to yield a compound or compounds represented by the structure shown in FIG. $BG_{1-1}$, below,

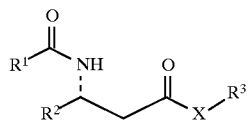

FIG. $BG_{1-1}$

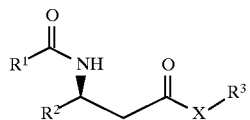

the compounds represented by $BG_1$ are dissolved in a suitable solvent, to which is added a compound represented by FIG. GRX, below,

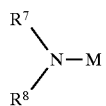

FIG. GRX where $R^7$ and $R^8$ are defined independently and are -($C_1$–$C_8$) alkyl, -($C_3$–$C_8$)cycloalkyl, -($C_1$–$C_8$)alkyl-($C_6$–$C_{12}$)aryl;

M is Li, Na, or K, the resulting dianion is then reacted with a compound represented by the structure shown in FIG. GYX,

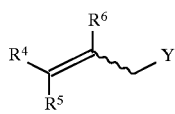

FIG. GYX where, $R^4$, $R^5$ and $R^6$ are defined independently and are H, -($C_1$–$C_8$)alkyl, -($C_3$–$C_8$)cycloalkyl, -($C_1$–$C_8$)alkyl-($C_3$–$C_8$) cycloalkyl, -($C_6$–$C_{12}$ aryl), -($C_1$–$C_8$)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl;

Y is halogen, —OTs, —OMs, or —OTf to produce a compound or compounds represented by FIG. $BG_{2-1}$

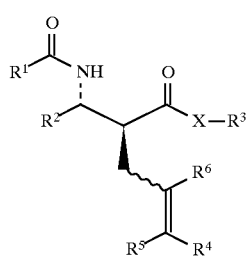

FIG. $BG_{2-1}$

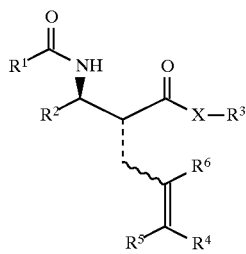

the compound or compounds represented by the structures in FIG. $BG_{2-1}$ are then used according to the process described below for the preparation of a compound or compounds represented by the structures on the left side, or the right side of FIG. BG4-1, below, or, if the starting materials are a racemic mixture, the reaction may produce a mixed ratio of compounds represented on both sides of the FIG. BG4-1, below,

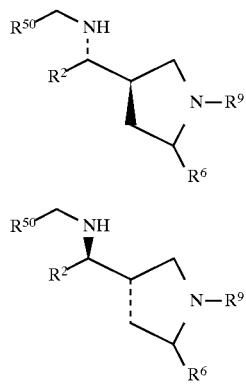

FIG. $BG_{4-1}$ where $R^{50}$ is H, -($C_1$–$C_8$)alkyl, -($C_3$–$C_8$)cycloalkyl, -($C_1$–$C_8$)alkyl-($C_3$–$C_8$)cycloalkyl, -($C_6$–$C_{12}$ aryl), -($C_1$–$C_8$) alkyl-($C_6$–$C_{12}$ aryl), or the aryl or alkyl is substituted with one to three of the following groups, ($C_6$–$C_{12}$ aryl), ($C_1$–$C_3$) alkyl, ($C_1$–$C_3$) alkoxy, halogen, trifluoromethyl.

When $R^1$ is —O—($C_{1-8}$ alkyl), —O—($C_{3-8}$ cycloalkyl), —O—($C_{1-8}$ alkyl)($C_{3-8}$ cycloalkyl), —O—($C_{6-12}$ aryl), —O—($C_{1-8}$ alkyl)-aryl, then reduction with LAH, DIBAL or Borane will always produce $R^{50}$ is H.

where $R^2$ is -($C_1$–$C_8$)alkyl, -($C_3$–$C_8$)cycloalkyl, -($C_1$–$C_8$) alkyl-($C_3$–$C_8$)cycloalkyl, -($C_6$–$C_{12}$ aryl), -($C_1$–$C_8$)alkyl-($C_6$–$C_{12}$ aryl), or the aryl or alkyl is substituted with one to three of the following groups, ($C_6$–$C_{12}$ aryl),($C_1$–$C_3$)alkyl, ($C_1$–$C_3$) alkoxy, halogen, trifluoromethyl; ($C_6$–$C_{12}$) aryl, where $R^6$ is H, -($C_1$–$C_8$)alkyl, -($C_3$–$C_8$)cycloalkyl, -($C_1$–$C_8$) alkyl-($C_3$–$C_8$)cycloalkyl, -($C_6$–$C_{12}$ aryl), -($C_1$–$C_8$)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl;

where $R^9$ is H, -($C_1$–$C_8$)alkyl, -($C_3$–$C_8$)cycloalkyl, -($C_1$–$C_8$) alkyl-($C_3$–$C_8$)cycloalkyl, -($C_6$–$C_{12}$ aryl), -($C_1$–$C_8$)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl;

comprising treating a compound or compounds represented by FIG. $BG_{3-1}$ with a reducing agent such as with LiAlH$_4$, DIBAL or Borane in a suitable solvent such as THF preceeded by the following process, a process for preparing a compound or compounds represented by FIG. $BG_{3-1}$

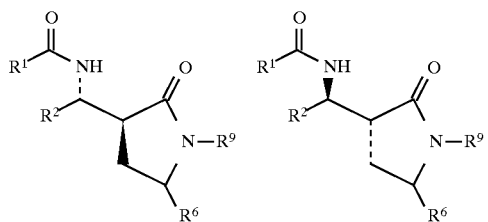

FIG. $BG_{3-1}$ where $R^1$ is H, -($C_1$–$C_8$)alkyl, -($C_3$–$C_8$)cycloalkyl, -($C_1$–$C_8$) alkyl-($C_3$–$C_8$)cycloalkyl, -($C_6$–$C_{12}$ aryl), -($C_1$–$C_8$)alkyl-($C_6$–$C_{12}$ aryl), —O—($C_{1-8}$ alkyl), —O—($C_{3-8}$ cycloalkyl), —O—($C_{1-8}$ alkyl)($C_{3-8}$ cycloalkyl), —O—($C_{6-12}$ aryl), —O—($C_{1-8}$ alkyl)-aryl, or the aryl or alkyl is substituted with one to three of the following groups, ($C_6$–$C_{12}$ aryl), ($C_1$–$C_3$)alkyl, ($C_1$–$C_3$) alkoxy, halogen, trifluoromethyl, where $R^2$ is -($C_1$–$C_8$)alkyl, -($C_3$–$C_8$)cycloalkyl, -($C_1$–$C_8$) alkyl-($C_3$–$C_8$)cycloalkyl, -($C_6$–$C_{12}$ aryl), -($C_1$–$C_8$)alkyl-($C_6$–$C_{12}$ aryl), or the aryl or alkyl is substituted with one to three of the following groups, ($C_6$–$C_{12}$ aryl),($C_1$–$C_3$)alkyl, ($C_1$–$C_3$) alkoxy, halogen, trifluoromethyl;
where $R^6$ is H, -($C_1$–$C_8$)alkyl, -($C_3$–$C_8$)cycloalkyl, -($C_1$–$C_8$) alkyl-($C_3$–$C_8$)cycloalkyl, -($C_6$–$C_{12}$ aryl), -($C_1$–$C_8$)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl;
where $R^9$ is H, -($C_1$–$C_8$)alkyl, -($C_3$–$C_8$)cycloalkyl, -($C_1$–$C_8$) alkyl-($C_3$–$C_8$)cycloalkyl, -($C_6$–$C_{12}$ aryl), -($C_1$–C8)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl;
which comprises subjecting to ozonolysis a compound or compounds represented by FIG. $BG_{2-1}$

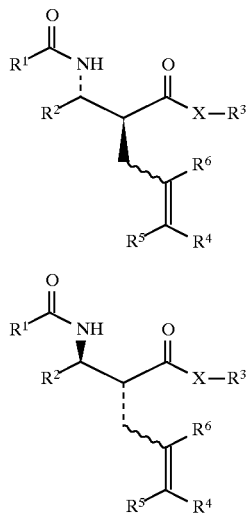

FIG. $BG_{2-1}$ where $R^3$ is -($C_1$–$C_8$)alkyl, -($C_3$–$C_8$)cycloalkyl, -($C_1$–$C_8$) alkyl-($C_3$–$C_8$)cycloalkyl, -($C_6C_{12}$ aryl), -($C_1$–$C_8$)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl, $R^4$, $R^5$ and $R^6$ are defined previously, X is O, NH, or S, followed by reaction with $R^9$—$NH_2$, under reducing conditions, such as with sodium cyano borohydride, sodium triacetoxy borohydride or sodium borohydride, (in order of preference) at 0°–50° C., or a cool temperature to control heat, to produce the desired compounds.

The invention also comprises the reactions of CHARTS C and D, summarized below.

The process for the preparation of a compound or of compounds represented by the structures on the left side, or the right side of FIG. $CG_3$, below, or, if the starting materials are a racemic mixture, the reaction may produce a mixed ratio of compounds represented on both sides of the FIG. $CG_3$, below,

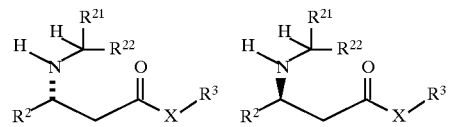

FIG. $CG_3$ which comprises, a series of reactions, beginning with an appropriate optically active amine represented by FIG. $CG$-$R_1$, below,

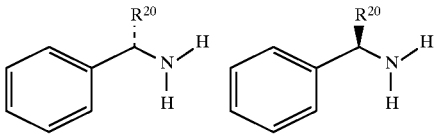

FIG. $CG$-$R_1$ where $R^{20}$ is -($C_1$–$C_8$)alkyl, -($C_3$–$C_8$)cycloalkyl, -($C_1$–$C_8$) alkyl-($C_3$–$C_8$)cycloalkyl, -($C_6$–$C_{12}$ aryl), -($C_1$–$C_8$)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl, is condensed with a carbonyl compound, such as one represented by the structure shown in FIG. $CG$-$R_2$ below,

FIG. $CG$-$R_2$ where $R^{21}$ and $R^{22}$ are defined independently and are H, -($C_1$–$C_8$)alkyl, -($C_3$–$C_8$)cycloalkyl, -($C_1$–$C_8$)alkyl-($C_3$–$C_8$) cycloalkyl, -($C_6$–$C_{12}$ aryl), -($C_1$–$C_8$)alkyl-($C_6$–$C_{12}$ aryl), or the alkyl is substituted with one to three of the following groups, -($C_6$–$C_{12}$ aryl), -($C_1$–$C_3$)alkyl, -($C_1$–$C_3$) alkoxy, halogen, trifluoromethyl; under reducing conditions using $NaBH_4$ or a similar suitable boron hydride reducing agent in a suitable solvent such as THF to obtain compounds represented by the structures shown in FIG. $CG_{1(b)}$ below,

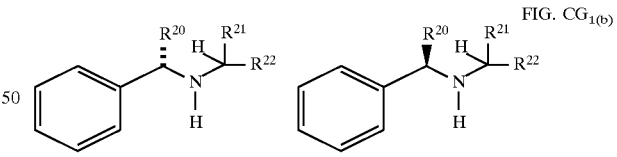

FIG. $CG_{1(b)}$ compounds represented by the deprotonated form of FIGS. $CG_{1(b)}$, above, then undergoes a Michael Addition reaction with a compound represented by the structure shown in FIG. $CG_{1(a)}$, below, A compound represented by the structures shown in $CG_{1(a)}$, below,

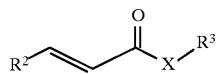

FIG. $CG_{1(a)}$ where, $R^2$ and $R^3$ are independently, lower alkyl, alkylaryl, or optionally substituted aryl, then deprotonation is carried out with an appropriate base such as n-BuLi, to produce compounds, after coupling, represented by the structures shown in FIG. $CG_2$ below,

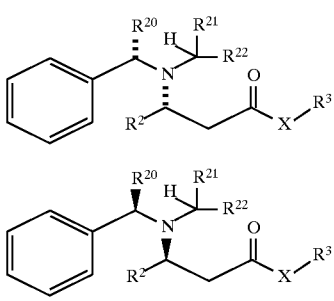

FIG. CG$_2$

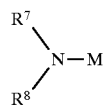

FIG. GRX where $R^7$ and $R^8$ are defined independently and are -($C_1$–$C_8$) alkyl, -($C_3$–$C_8$)cycloalkyl, -($C_1$–$C_8$)alkyl-($C_6$–$C_{12}$)aryl; where M is Li, Na, or K; and the resulting anion or dianion is then reacted with a compound represented by the structure shown in FIG. DG-R$_2$ below,

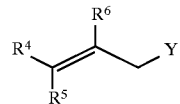

FIG. DG-R$_2$ where $R^4$, $R^5$, and $R^6$ are independent and are H, alkyl, alkylaryl, or optionally substituted aryl, and where Y is halogen, —OTs, —OMs, or —OTf; to obtain a compound represented by the structures shown in FIG. DG$_1$, below.

the carbon nitrogen bonds are hydrogenolytically cleaved with an appropriate reducing agent such as Pearlman's catalyst, 20 percent palladium hydroxide on charcoal, in an appropriate solvent, such as EtOH, to obtain the desired compounds. Products of the reactions of CHART C are then used in the reactions of CHART D, summarized below. Note that the compounds represented by FIG. CG$_3$ are the same as those represented by FIG. DG$_0$.

The process for the preparation of a compound or the compounds represented by the structures on the left side, or the right side of FIG. DG$_7$, below, or, if the starting materials are a racemic mixture, the reaction may produce a mixed ratio of compounds represented on both sides of the FIG. DG$_7$, below,

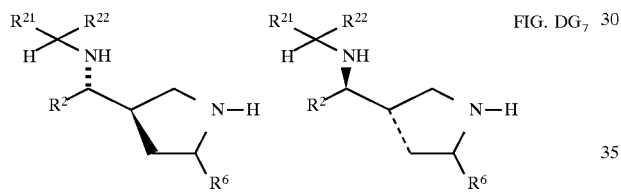

FIG. DG$_7$ which comprises a series of reactions, the reactions beginning with a compound represented by the structures in FIGS. DG$_0$, below,

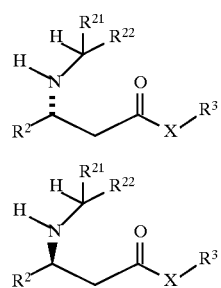

FIG. DG$_0$ where $R^2$ and $R^3$ are defined independently and are lower alkyl, alkylaryl, or optionally substituted aryl; where $R^{21}$ and $R^{22}$ are defined independently and are H, -($C_1$–$C_8$)alkyl, -($C_3$–$C_8$)cycloalkyl, -($C_1$–$C_8$)alkyl-($C_3$–$C_8$)cycloalkyl, -($C_6$–$C_{12}$ aryl), -($C_1$–$C_8$)alkyl-($C_6$–$C_{12}$ aryl),-or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl; and where X is O, NH, S; are dissolved in a suitable organic solvent such as tetrahydrofuran, and then added, in a cool temperature to control exothermic formations under an inert atmosphere, such as between a temperature of −50° C. and 0° C. in a nitrogen atmosphere, to a solution of a compound of the description in FIG. GRX, dissolved in a suitable organic solvent,

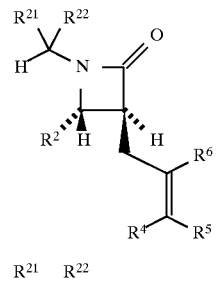

FIG. DG$_1$ the compounds represented by the structures shown in FIG. DG$_1$ are subjected to an established method of ozonolysis, such as bubbling O$_3$ from an ozone generator, such as a Welsbach ozonator, through the reaction mixture in an appropriate solvent, such as water or methanol, followed by reduction of the intermediate ozonide with an appropriate boron hydride reducing agent such as NaBH$_4$ or LiBH$_4$ to obtain a compound represented by the structures shown in FIG. DG$_2$ , below,

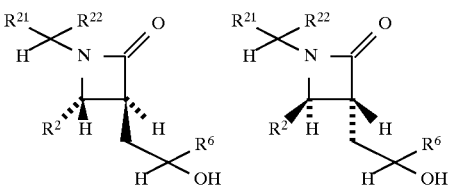

FIG. DG$_2$ the compounds represented by the structures shown in FIG. DG$_2$ are treated with an appropriate amine base, such as triethylamine, and an activating agent, such as methanesulfonyl chloride in a solvent such as tetrahydrofuran or toluene to obtain a compound represented by the structures shown in FIG. DG$_3$, below,

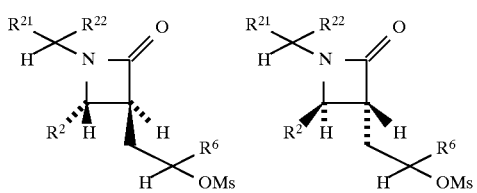

where Ms is mesylate, the compounds represented by the structures shown in FIG. DG$_3$ are treated in an appropriate solvent such as toluene or THF with an amine represented by the structure shown in FIG. DG-R$_1$ below,

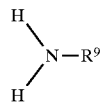

FIG. DG—R$_1$ where R$^9$ is H, -(C$_1$–C$_8$)alkyl, -(C$_3$–C$_8$)cycloalkyl, -(C$_1$–C$_8$) alkyl-(C$_3$–C$_8$)cycloalkyl, -(C$_6$–C$_{12}$ aryl), -(C$_1$–C$_8$)alkyl-(C$_6$–C$_{12}$ aryl), or the aryl or alkyl is substituted with one to three of the following groups, -(C$_6$–C$_{12}$ aryl), -(C$_1$–C$_3$)alkyl, -(C$_1$–C$_3$) alkoxy, halogen, trifluoromethyl; to obtain a compound represented by the structures shown in FIG. DG$_4$ below,

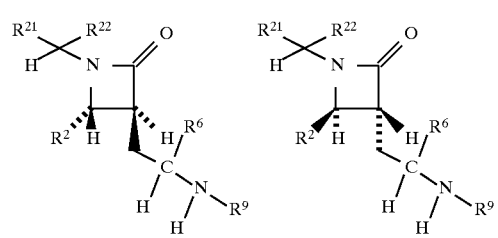

the compounds represented by the structures shown in FIG. DG$_4$ undergo thermal isomerization to give a compound represented by the structures shown in FIG. DG$_5$, below,

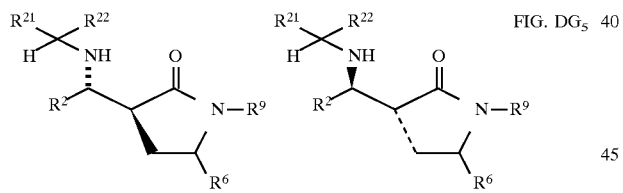

the compounds represented by the structures shown in FIG. DG$_5$ are treated with a suitable reducing agent such as LiAlH$_4$, DIBAL or borane in a suitable solvent such as THF to obtain a compound represented by the structures shown in FIG. DG$_6$, below,

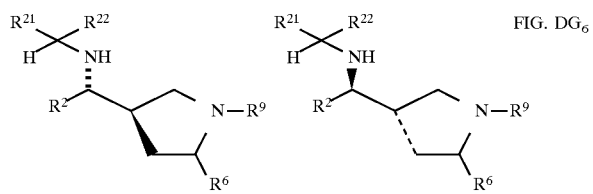

when R$^9$ is a protective group, where, for example, an alkylaryl is connected to the nitrogen atom with one carbon atom between the nitrogen and the aryl, then the compounds represented by the structures shown in FIG. DG$_6$ may be hydrogenolytically cleaved with, for example, 20 percent palladium hydroxide on charcoal, H$_2$ to obtain the desired compound or compounds.

Another series of reactions, similar to those in CHART C and CHART D are also claimed in this invention, those are from the reactions of CHART E and CHART F, below.

Also claimed is a process for the preparation of compounds represented by the structures on the left side, or the right side of FIG. FG$_6$, below, or, if the starting materials are a racemic mixture, the reaction may produce a mixed ratio of compounds represented on both sides of the FIG. FG$_6$, below,

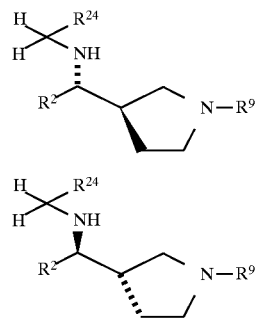

FIG. FG$_6$ which comprises a series of reactions, the reactions beginning with a compound represented by the structures in FIGS. EG-R$_1$, below,

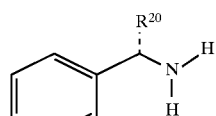

FIG. EG-R$_1$

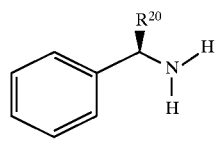

where R$^{20}$ is -(C$_1$–C$_8$)alkyl, -(C$_3$–C$_8$)cycloalkyl, -(C$_1$–C$_8$) alkyl-(C$_3$–C$_8$)cycloalkyl, -(C$_6$–C$_{12}$ aryl), -(C$_1$–C$_8$)alkyl-(C$_6$–C$_{12}$ aryl), or the aryl or alkyl is substituted with one to three of the following groups, -(C$_6$–C$_{12}$ aryl), -(C$_1$–C$_3$)alkyl, -(C$_1$–C$_3$) alkoxy, halogen, trifluoromethyl; is condensed with a compound represented by the structure shown in FIG. EG-R$_2$ below, $$R^{24}\underset{O}{\overset{O}{\parallel}}\!\!\!\!\!\!\!\!\!\!\!\!C\!\!-\!\!O\!\!-\!\!R^{23}$$

FIG. EG-R$_2$ where R$^{23}$ is -(C$_1$–C$_8$)alkyl, -(C$_3$–C$_8$)cycloalkyl, -(C$_1$–C$_8$) alkyl-(C$_3$–C$_8$)cycloalkyl, -(C$_6$–C$_{12}$ aryl), -(C$_1$–C$_8$)alkyl-(C$_6$–C$_{12}$ aryl), or the aryl or alkyl is substituted with one to three of the following groups, -(C$_6$–C$_{12}$ aryl), -(C$_1$–C$_3$)alkyl, -(C$_1$–C$_3$) alkoxy, halogen, trifluoromethyl;

where R$^{24}$ is H, -(C$_1$–C$_8$)alkyl, -(C$_3$–C$_8$)cycloalkyl, -(C$_1$–C$_8$)alkyl-(C$_3$–C$_8$)cycloalkyl, --(C$_6$–C$_{12}$ aryl), -(C$_1$–C$_8$)alkyl-(C$_6$–C$_{12}$ aryl), or the aryl or alkyl is substituted with one to three of the following groups, -(C$_6$–C$_{12}$ aryl), -(C$_1$–C$_3$)alkyl, -(C$_1$–C$_3$) alkoxy, halogen, trifluoromethyl; to obtain a compound represented by the structures shown in FIG. EG$_{1(b')}$, below,

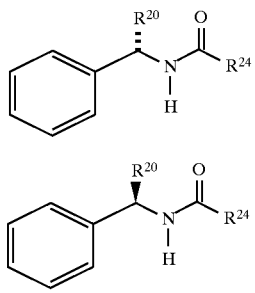

FIG. EG$_{1(b')}$ which is treated with an appropriate reducing agent such as LiAlH$_4$, DIBAL or Borane in a suitable solvent such as THF to obtain compounds represented by the structures shown in FIG. EG$_{1(b)}$, below.

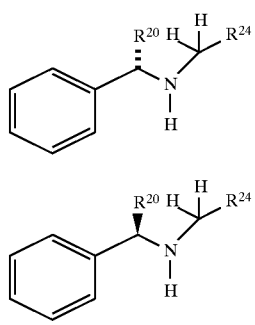

FIG. EG$_{1(b)}$ the compounds represented by the structures shown in EG$_{1(a)}$, below,

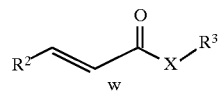

FIG. EG$_{1(a)}$ where R$^2$ are R$^3$ are independently, lower alkyl, arlkylaryl, or optionally substituted aryl, then undergoes a Michael Addition reaction with a compound represented by the deprotonated form of the structures shown in FIG. EG$_{1(b)}$, (the deprotonation is carried out with an appropriate base such as n-BuLi) to produce compounds, after coupling, represented by the structures shown in FIG. EG$_2$, below,

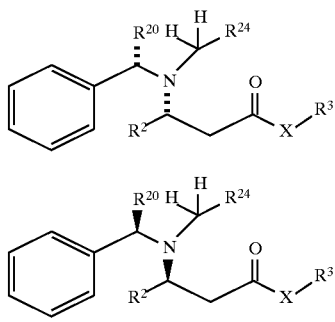

FIG. EG$_2$ the compounds represented by the structures shown in FIG. EG$_2$ have carbon nitrogen bonds that are hydrogenolytically cleaved with an appropriate reducing agent such as Peariman's catalyst, 20 percent palladium hydroxide on charcoal, in an appropriate solvent, such as EtOH, to obtain the compounds represented by the structures shown in FIG. EG$_3$, same figure as FG$_0$, below,

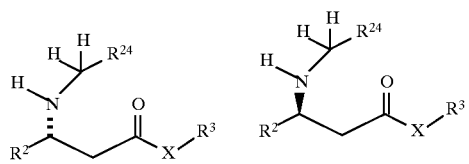

FIG. EG$_3$ = FIG. FG$_0$ where R$^2$, R$^3$, R$^{24}$ and X are defined above); is dissolved in a suitable organic solvent such as tetrahydrofuran, and added, in a cool temperature to control exothermic formations under an inert atmosphere, such as, between a temperature of –50° C. and 0° C. in a nitrogen atmosphere, to a solution of a compound represented by the structures shown in FIG. GRX, below,

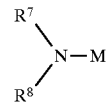

FIG. GRX where R$^7$ and R$^8$ are defined independently and are -(C$_1$–C$_8$) alkyl, -(C$_3$–C$_8$)cycloalkyl, -(C$_1$–C$_8$)alkyl-(C$_6$–C$_{12}$)aryl; and M is Li, Na, or K;

the resulting anion or dianion is then reacted with a compound represented by the structures shown in FIG. FG-R$_2$, below,

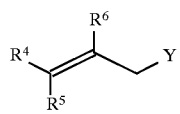

FIG. FG-R$_2$ where R$^4$, R$^5$, and R$^6$ are independent and are H, alkyl, alkylaryl, or optionally substituted aryl, and where Y is halogen, —OTs, —OMs, or —OTf; to obtain a compound represented by the structures shown in FIG. FG$_1$, below,

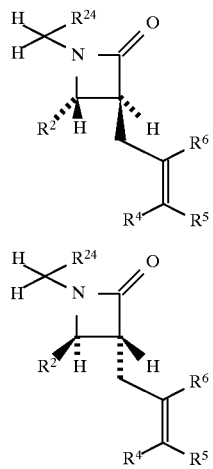

FIG. FG$_1$ the compounds represented by the structures shown in FIG. FG$_1$, are subjected to an established method of ozonolysis, such as bubbling O$_3$ from an ozone generator, such as a Welsbach ozonator, through the reaction mixture in an appropriate solvent such as water or methanol, followed by treatment of the intermediate ozonide with an appropriate boron hydride reducing agent such as NaBH$_4$ or LiBH$_4$ to obtain a compound represented by the structures shown in FIG. FG$_2$, below,

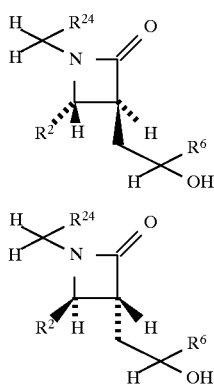

FIG. FG$_2$ the compounds represented by the structures shown in FIG. FG$_2$ are treated with an appropriate amine base, such as triethylamine, and methanesulfonyl chloride in a solvent such as tetrahydrofuran or toluene to obtain a compound represented by the structures shown in FIG. FG$_3$, below,

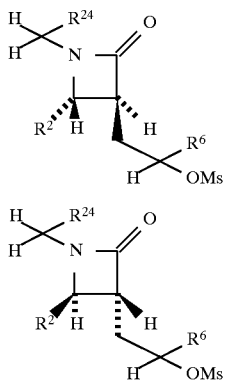

FIG. FG$_3$ the compound or compounds represented by the structures shown in FIG. FG$_3$, where Ms is mesylate, are treated in an appropriate solvent such as toluene or THF with an amine represented by the structure shown in FIG. FG-R$_1$ below,

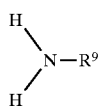

FIG. FG-R$_1$ where R$^9$ is H, -(C$_1$–C$_8$)alkyl, -(C$_3$–C$_8$)cycloalkyl, -(C$_1$–C$_8$) alkyl-(C$_3$–C$_8$)cycloalkyl, -(C$_6$–C$_{12}$ aryl), -(C$_1$–C$_8$)alkyl-(C$_6$–C$_{12}$ aryl), or the aryl or alkyl is substituted with one to three of the following groups, -(C$_6$–C$_{12}$ aryl), -(C$_1$–C$_3$)alkyl, -(C$_1$–C$_3$) alkoxy, halogen, trifluoromethyl; to obtain a compound represented by the structures shown in FIG. FG$_4$ below,

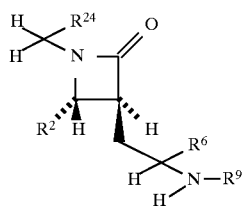

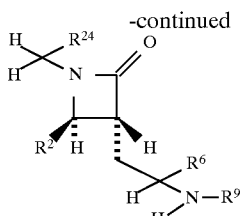

the compounds represented by the structures shown in FIG. FG$_4$ thermally isomerizes to give a compound represented by the structures shown in FIG. FG$_5$ below,

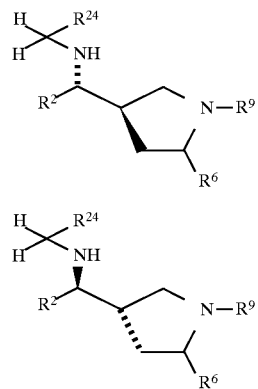

FIG. FG$_5$ the compound or compounds represented by the structures shown in FIG. FG$_5$ are treated with a suitable reducing agent such as LiAlH$_4$, DIBAL or Borane in a suitable solvent such as THF to obtain the desired compounds.

These reactions and processes are of course designed to be used with specific reactants to produce specific products same of these specific reactions and products are described more completely herein.

DETAILED DESCRIPTION OF THE INVENTION

The compounds of this invention are identified by both descriptive names and by reference to structures shown in appropriate charts and text. In appropriate situations, the proper stereochemistry, an important aspect of this invention is also represented in the charts.

The compounds and processes of this invention may be divided into two groups. The four groups are described in CHARTs A, and B. Within each group the reactions are shown as steps. CHARTs AG and BG are generic charts, various substituted R groups are indicated. The steps from CHARTs AG and BG are generic steps that describe reactions that are specified to the degree needed to enable one ordinarily skilled in the art to practice the invention. Following the general procedures for each group are one or more detailed preparations and examples that describe precisely how to prepare specific compounds of this invention. CHART AX1 thus describes the experimental steps for one specific reaction sequence described in CHART AG and BX1 shows a specific reaction from CHART BG. Note that the generic charts as well as the specific reactions show the stereochemistry of the compounds. The specific procedures are to be construed as merely illustrative, and do not impose limitations upon the general reaction schemes in any manner whatsoever. Those skilled in the art will promptly recognize appropriate variations from the procedures both as to reactants as well as to reaction conditions and techniques.

DEFINITIONS

The following words or abbreviations are used to describe this invention. The definitions and examples provided below are intended to provide guidance and illustration for procedures and methods described herein but are not intended to impose limitations upon the subject matter described.

Variables defined

In this document the parenthetical term $(C_n-C_m)$ is inclusive such that a compound of $(C_1-C_8)$ would include compounds of one to 8 carbons and their isomeric forms. The various carbon moieties are defined as follows:

Alkyl refers to an aliphatic hydrocarbon radical and includes branched or unbranched forms such as methyl, ethyl, n-propyl, isopropyl, n-butyl, isobutyl, sec-butyl, t-butyl, n-pentyl, isopentyl, n-hexyl, isohexyl, n-heptyl, isoheptyl, and n-octyl, etc.

Lower alkyl refers to alkyl compounds that includes 1 to 8 carbons, $C_1-C_8$ and their isomeric forms.

Alkoxy, as represented by $-OR_X$ when $R_X$ is a $(C_1-C_8)$ alkyl, refers to an alkyl radical which is attached to the remainder of the molecule by oxygen and includes branched or unbranched forms such as methoxy, ethoxy, n-propoxy, isopropoxy, n-butoxy, isobutoxy, sec-butoxy, t-butoxy, n-pentoxy, isopentoxy, n-hexoxy, isohexoxy, n-heptoxy, isoheptoxy, and n-octoxy.

Aryl refers to aromatic hydrocarbon radicals that contain 6 to 12 carbon atoms such as phenyl, α-naphthyl, β-naphthyl, m-methylphenyl, p-trifluoromethylphenyl and the like. The aryl groups can also be substituted with one to three of any of the following groups: $C_1-C_3$ alkoxy, $C_1-C_3$ alkyl, trifluoromethyl, halogen.

Alkylaryl refers to an alkyl, as defined above, attached to an aryl, as defined above. A moiety expressed as "lower alkylaryl" could also be expressed as "$(C_1-C_8)$alkylaryl" the alkyl portion would be attached to the molecule of interest. Benzyl for example would be an unsubstituted $C_1$ alkylaryl.

Aryloxy refers to an aryl radical, as described above, which is attached to the remainder of the molecule by oxygen.

Arylalkoxy refers to an aryl radical, as described above, which is attached to an alkyl, as described above, which is attached to the remainder of the molecule by oxygen.

Cycloalkyl refers to a radical of a saturated cyclic hydrocarbon containing 3 to 10 carbon atoms, $(C_3-C_{10})$ cycloalkyl, such as cyclopropyl, cyclobutyl, cyclopentyl, cyclohexyl, cycloheptyl, cyclooctyl, cyclononyl and cyclodecyl. The term also includes alkyl-substituted cycloalkyl, such as 2-methylcyclopropyl, 2,2-dimethylcyclopropyl, 2,3 diethylcyclopropyl, 2-butylcyclopropyl, cyclobutyl, 2-methylcyclobutyl, 3-propylcyclobutyl, 2,2-dimethylcyclopentyl.

Cycloalkoxy refers to a cycloalkyl, as described above, which is attached to the remainder of the molecule by oxygen.

Halogen or Halo refers to the halogens which include fluorine, chlorine, bromine and iodide.

Constants defined

BnO is benzyloxy. DIBAL is Diisobutyl Aluminum Hydride. Borane may refer to any borane, $BH_3$, and related reagents such as diborane, $B_2H_6$. Boron hydride reducing agents are exemplified by such reagents as $LiBH_4$ and $NaBH_4$. °C. is degree Centigrade. Celite or Celite Pad is commercially available filter aid. $Et_2O$ is diethyl ether. EtOAc is ethyl acetate. g is gram. $H_2$ is hydrogen gas. Hx is hexane. HCl - Hydrochloric acid. i-$Pr_2$NH is diisopropylamine. L is liter. LAH or $LiAlH_4$ is Lithium Aluminum Hydride. LDA is Lithium Diisopropyl Amide. M is Molar. Mol. is mole. mg is milligram. $MgSO_4$ is Magnesium Sulphate. min. is minute. mL is milliliter. mM is milliMole. Ms is mesylate. N is Normality of solution, where appropriate. N is Nitrogen atom where appropriate, $N_2$ is nitrogen gas or atmosphere. $N_3$ is azide or azido or azido carboxy compound. NMR is Nuclear Magnetic Resonance. NaOH is Sodium Hydroxide. $NaCNBH_3$ is Sodium Cyano Borohydride. O is Oxygen. OEt is ethoxy. —OMs is methylsulfonate or mesylate. —OTf is trifluoromethylsulfonate or triflate. —OTs is p-toluenesulfonate or tosylate. "Pearlman's" catalyst is 10 percent Palladium Hydroxide on charcoal. psi is pounds per square inch. n-BuLi is n-Butyllithium. RT or R.T. is room temperature. S is Sulphur. S-aryl is a thioaryl compound. $SiO_2$ is Silica gel. Strong hydride reducing agents are exemplified by such reagents as DIBAL, LAH, and Borane. t-BuOH is tertiary butyl alcohol. THF is tetrahydrofuran. "Welsbach ozonator" is an example of an ozone generating device. Any suitable ozone generating device may be used in the operation of this invention.

Temperature and atmosphere considerations. Many reactions in this invention are performed under cooler conditions to better cope with heat generated during the reaction (exothermic formations). The deprotonation reactions are typical of this type of exothermic reaction. These deprotonation reactions are usually run at 0° to –50° C., this is the preferred range using the reactants used here. This is not to say that the reaction must be run at this range, indeed, many of the deprotection reactions could be run anywhere from room temperature down to below –100° C. When the atmosphere is described it is intended to provide a preferred method of running the reaction. The Michael Addition reactions, among others, have fewer side reactions when they are run under an atmosphere that excludes water. Thus reactions run under nitrogen gas could also be run under argon gas or other suitable inert or nonreactive gases that would operate to exclude side reactions with water. The Michael Addition reactions also have greater selectivity when they are run at lower temperatures. Thus the preferred range for a Michael Addition is about –70° to –80° C., but this reaction can be run from room temperature to below –100° C., but the selectivity declines appreciably at higher temperatures.

The best mode of performing the reactions appears to be according to the procedures found in CHARTS E and CHARTS F.

THE REACTIONS AND COMPOUNDS OF THE CHARTS

The reactions of this invention are grouped in various CHARTS. The CHARTS are logical groupings of sequential reactions. The word CHART indicates the written procedures, including what is commonly known in the art and obvious variants thereof, as well as the specific flow charts containing images or drawings suggesting chemical structures. Sometimes the product of the reactions in one CHART will be used as the starting material for the reaction in another CHART. In this manner CHARTS A and B are related, CHARTS C and D are related, and CHARTS E and F are related. CHARTS A, C and E describe three different procedures for making similar compounds, as do CHARTS B, D, and E. The CHARTS are named sequentially by the letters A–E, the letter "G" in the CHART indicates the CHART shows a general scheme, with structures containing variables. The letter "X" in the name of the CHART indicates it is a specific reaction with X meaning an specific embodiment or example. Thus CHART AG shows generically how to make many compounds, the products of this CHART could be used as starting material for CHART BG and representational embodiments are shown in CHARTS AX1, AX2, BX1, BX2, etc.

THE REACTIONS AND COMPOUNDS OF CHART A

CHART AG shows the general reaction scheme and the major reaction Steps of the reactions involved in the synthesis of the compounds of CHART A. CHART AX1 shows a specific reaction scheme for a single specific compound that is generally described in CHART A. The final compounds produced by the descriptions for CHART A are used as the starting materials for the reactions of CHART B. A description of the Steps and procedures from the compounds and reactions shown in CHARTs AG and AX1 appear below, followed by CHART AG and CHART AX1. The reactions and compounds of CHART B follows this section.

THE STEPS OF CHART AG

The starting materials utilized to prepare the compounds of this invention are either available commercially or can be prepared by the following methods.

Step 1(a). $AG_0 \rightarrow AG_{1(a)}$.

A compound represented by the structure shown in FIG. $AG_0$, below

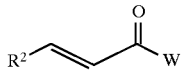

FIG. $AG_0$ where $R^2$ is $-(C_1-C_8)$alkyl, $-(C_3-C_8)$cycloalkyl, $-(C_1-C_8)$alkyl-$(C_3-C_8)$cycloalkyl, $-(C_6-C_{12}$ aryl), $-(C_1-C_8)$alkyl-$(C_6-C_{12}$ aryl), or the aryl or alkyl is substituted with one to three of the following groups, $(C_6-C_{12}$ aryl),$(C_1-C_3)$alkyl, $(C_1-C_3)$ alkoxy, halogen, trifluoromethyl; and W is $C_1$, Br, -$SR^2$ or

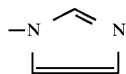

is treated with $R^3XLi$ where $R^3$ is $-(C_1-C_8)$alkyl, $-(C_3-C_8)$cycloalkyl, $-(C_1-C_8)$alkyl-$(C_3-C_8)$cycloalkyl, $-(C_6-C_{12}$ aryl), $-(C_1-C_8)$alkyl-$(C_6-C_{12}$ aryl), or the aryl or alkyl is substituted with one to three of the following groups, $-(C_6-C_{12}$ aryl), $-(C_1-C_3)$alkyl, $-(C_1-C_3)$ alkoxy, halogen, trifluoromethyl; and X is O, NH, S, to obtain a compound represented by the structure shown in FIG. $AG_{1(a)}$, below

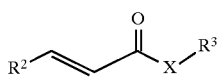

FIG. $AG_{1(a)}$

Step 1(b). Amide+aldehyde$\rightarrow AG_{1(b)}$.

An appropriate optically active amine and an appropriate aldehyde, below, are reacted under reducing conditions using $NaBH_4$ or a similar suitable boron hydride reducing agent to produce the compound represented by the structure shown in FIG. $AG_{1(b)}$, below,

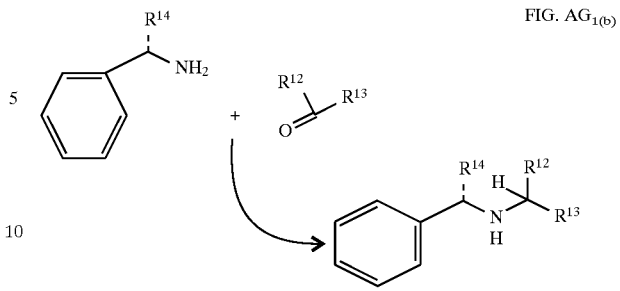

FIG. $AG_{1(b)}$ where $R^{12}$ is $(C_6-C_{12}$ aryl), or the aryl is substituted with one to three of the following groups, $(C_1-C_3)$alkyl, $(C_1-C_3)$ alkoxy, halogen, trifluoromethyl;
$R^{13}$ is H, $-(C_1-C_8)$alkyl, $-(C_3-C_8)$cycloalkyl, $-(C_1-C_8)$alkyl-$(C_3-C_8)$cycloalkyl, $-(C_6-C_{12}$ aryl), $-(C_1-C_8)$alkyl-$(C_6-C_{12}$ aryl), or the aryl or alkyl is substituted with one to three of the following groups, $-(C_6-C_{12}$ aryl), $-(C_1-C_3)$alkyl, $-(C_1-C_3)$ alkoxy, halogen, trifluoromethyl,
where $R^{14}$ is $-(C_1-C_8)$alkyl, $-(C_3-C_8)$cycloalkyl, $-(C_1-C_8)$ alkyl-$(C_3-C_8)$cycloalkyl, $-(C_6-C_{12}$ aryl), $-(C_1-C_8)$alkyl-$(C_6-C_{12}$ aryl), or the aryl or alkyl is substituted with one to three of the following groups, $-(C_6-C_{12}$ aryl), $-(C_1-C_3)$alkyl, $-(C_1-C_3)$ alkoxy, halogen, trifluoromethyl.

Step 2. $AG_{1(a)}+AG_{2(b)}\rightarrow AG_2$.

A compound represented by the structure shown in FIG. $AG_{1(a)}$ is reacted with a compound represented by the deprotonated form of the structure shown in FIG. $AG_{1(b)}$. Deprotonation is carried out with an appropriate base such as n-BuLi, to produce the compounds represented by the structures shown in FIG. $AG_2$, below,

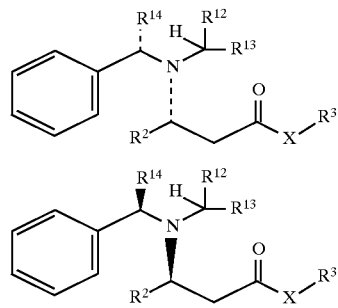

FIG. $AG_2$

Step 3. $AG_2 \rightarrow AG_3$.

Since $R^{12}$ is aryl, the nitrogen may be deprotected. The carbon nitrogen bonds are hydrogenolytically cleaved with an appropriate reducing agent such as Pearlman's catalyst, 10 percent paladium hydroxide on charcoal, to obtain the compounds represented by the structure shown in FIG. $AG_3$, below.

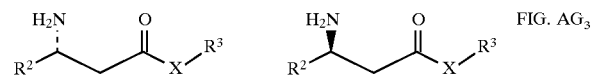

FIG. $AG_3$

Compounds represented by the structure shown in FIG. $AG_3$ can then be used in the reactions of CHART B.

EXAMPLES FROM CHART A–CHART AX1

The specific procedures and examples described below, shown in CHART AX1 are to be construed as merely illustrative of the procedure described above, and do not impose limitations upon the general reaction schemes in any manner whatsoever. Those skilled in the art will promptly recognize appropriate variations from the procedures both as to reactants as well as to reaction conditions a nd techniques.

Step 1(a). Preparation of t-butyl crotonate.

The starting materials for this step are commercially available. Shown above is Crotyl chloride and the product t-butyl crotonate.

A solution of t-BuOH (0.50 mol, 37.1 g, 47.8 mls) in THF (500 mls) is cooled to 5° C.; then over a 30 minute period n-BuLi (0.56 mol., 350 ml, 1.6M) is added to the solution. The resulting mixture is stirred for 40 minutes at room temperature. Crotyl chloride (0.50 mol., 52.3 g, 47.9 mls) in THF (250 mls) is added to the reaction mixture at room temperature over a 15 minute period. The resulting mixture is heated under reflux for 50 minutes. The reaction mixture is cooled to 0° C. and ice-water (800 mls) is added. The layers are separated and the aqueous layer is extracted with Et$_2$O (3×600 mls). The organic phases are combined, dried over Na$_2$SO$_4$, filtered and concentrated by rotary evaporation to give a red oil. Distillation (55° C., 22 mm) yields t-butyl crotonate: $^1$H NMR (300 MHz, CDCl$_3$) δ 1.46 (s, 9H), 1.83 (dd, J is 6.9, 1.7 Hz, 3H), 5.74 (dq, J is 15.5, 1.7 Hz, 1H), 6.85 (dq, J is 15.5, 6.9 Hz, 1H).

Step 1(b). Preparation of S-benzyl-α-methylbenzylamine.

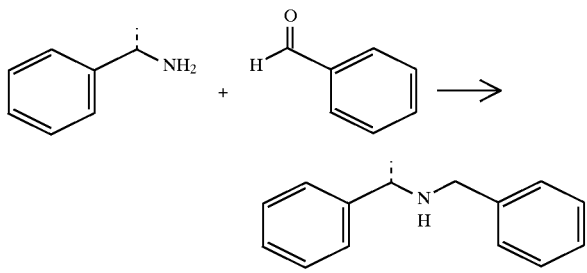

S-α-methylbenzylamine (4 0 g, 0.33 mol.) and benzaldehyde (35.5 g, 0.33 mol.) are combined in toluene (500 mls). The reaction mixture is refluxed until a constant amount of H$_2$O (5.2 ml) collects in a Dean-Stark trap. The reaction m mixture is concentrated by rotary evaporation to yield a light yellow liquid (89.2 g) which is dissolved in ethanol (350 ml). NaBH$_4$ (12.5 g, 0.33 mol.) is added portion-wise to the reaction mixture over a one hour period. The reaction mixture is stirred at room temperature for one hour and then cooled to 0° C. 2N HCl is added dropwise over a 2-hour period to the cold reaction mixture. The reaction mixture is concentrated by rotary evaporation and the residue is partitioned between EtOAc (200 ml) and H$_2$O (100 ml). The layers are separated and the aqueous layer is back-extracted with EtOAc (2×100 mls). The organic layers are combined, dried over MgSO$_4$ and concentrated by rotary evaporation to yield a light yellow oil. Distillation (115° C., 0.75 mm Hg) yields S-benzyl-α-methylbenzylamine: $^1$H NMR (300 MHz, CDCl$_3$) δ 1.37 (d, J is 6.6 Hz, 3H), 3.60 (d, J is 13.1 Hz, 1H), 3.66 (d, J is 13.1 Hz, 1H), 3.81 (q, J is 6.6 Hz, 1H), 7.23–7.36 (m, 10H).

Step 2. Preparation of t-butyl (S,S)-3-((N-benzyl)(N-methylbenzyl))aminobutyrate.

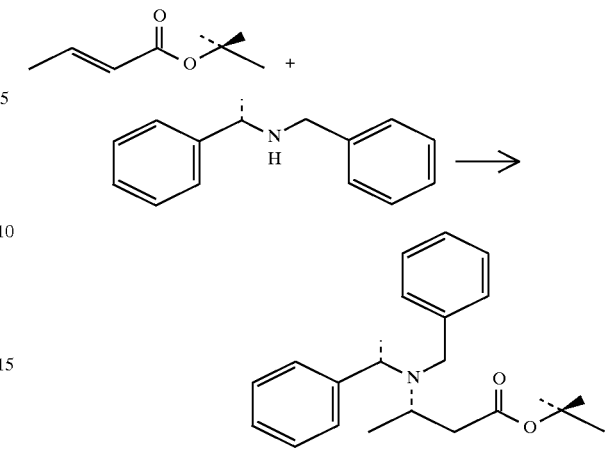

n-BuLi (158 ml, 0.25 mol.) is added via canula to a solution of S-benzyl-α-methylbenzylamine (53.5 g, 0.25 mol.) in THF (400 mls) at 0° C. under N$_2$. The reaction mixture is stirred for 15 minutes and then cooled to −78° C. t-Butyl crotonate (18.0 g, 0.13 mmol) dissolved in THF (150 ml) is added via canula to the −78° C. reaction mixture over a 40-minute period. Twenty minutes after the last of the t-Butyl crotonate is added, the reaction mixture is quenched with saturated aqueous NH$_4$Cl (100 mls), then saturated aqueous NaC$_1$(300 mls) is added. The layers are separated and the aqueous layer is extracted with ether (2×200 ml). The combined organic layers are washed with brine (100 mls), dried over MgSO$_4$, filtered and concentrated by rotary evaporation. The crude oil (72.72 g) is taken up in hexane (500 mls) and washed with 10% aqueous citric acid (buffered to pH 4, 100 ml portions) until all of the secondary amine is extracted from the organic phase. The organic phase is dried over MgSO$_4$, filtered and concentrated to yield t-butyl (S,S)-3-((N-benzyl)(N-methylbenzyl)) aminobutyrate: $^1$H NMR (300 MHz, CDCl$_3$) δ 1.09 (d, J is 6.7 Hz, 3H), 1.31 (d, J is 6.9 Hz, 3H), 1.37 (s, 9H), 2.00 (dd, J is 14.1, 9.1 Hz, 1H), 2.23 (dd, J is 14.1, 4.7 Hz, 1H), 3.41 (m, 1H), 3.60 (d,J is 15.0 Hz, 1H), 3.74 (d, J is 15.0 Hz, 1H), 3.87 (q, J is 7.0 Hz, 1H), 7.19–7.40 (m, 10H).

Step 3. Preparation of t-butyl (S)-3-aminobutyrate.

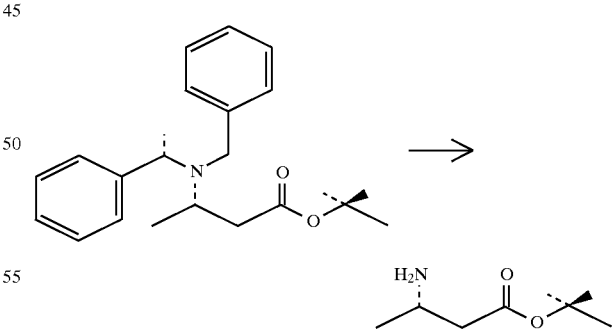

t-butyl (S,S)-3-((N-benzyl)(N-methylbenzyl)) aminobutyrate (36.5 g, 0.103 mol.) is dissolved in MeOH (500 mls). Pearlman's catalyst (5.25 g) is added and the reaction vessel is pressurized to 30 psi of H$_2$. After shaking for 24 hours, the reaction mixture is filtered through celite. The methanol is removed by distillation. The crude product is distilled (29 mm, 80°–96° C.) to yield S-t-butyl-β-aminobutyrate: $^1$H NMR (300 MHz, CDCl$_3$) δ 1.17 (d, J is 6.5 Hz, 3H), 1.45 (s, 9H), 2.38 (dd, J is 16.0, 8.2 Hz, 1H), 2.32 (broad s, 2H), 2.29 (dd, J is 16.0, 4.7 Hz, 1H), 3.39 (m, 1H). $[\alpha]_D^{25}$ is +19.5° (c 1.65, MeOH).

CHART AX2. Using the procedures above, a more preferred starting material is to substitute ethyl crotonate for t-butyl crotonate, see step 1(a). Then, following the above procedures, prepare ethyl (S,S)-3-((N-benzyl)(N-methylbenzyl))aminobutyrate, $^1$H NMR (300 MHz, CDCl$_3$) δ 1.14 (d, J is 7, 3H), 1.16 (t, J is 7, 3H), 1.34 (d, J is 7, 3H), 2.10 (dd, J is 14, 8, 1H), 2.35 (dd, J is 14, 6, 1H), 3.43 (ddq, J is 6, 8, 7, 1H), 3.68 (d, J is 15, 1H), 3.73 (d, J is 15, 1H), 3.89 (q, J is 7, 1H), 3.92 (dq, J is 11, 7, 1H), 4.02 (dq, J is 11, 7, 1H);

in step 2 instead of t-butyl (S,S)-3-((N-benzyl)(N-methylbenzyl))aminobutyrate and finally, in step 3, prepare ethyl (S)-3-aminobutyrate instead of t-butyl (S)-3-aminobutyrate.

CHARTAX3. Using the procedures above only starting with methyl crotonate, methyl (S)-3-amtinobutyrate has also been prepared. The ethyl (S)-3-aminobutyrate is slightly preferred over the methyl (S)-3-aminobutyrate. The ethyl (S)-3-aminobutyrate shown as one example in the reactions of CHARTB, the compound is shown in CHARTBX1.

THE REACTIONS AND COMPOUNDS OF CHART B

CHART B shows the general reaction scheme and the major reaction Steps of the reactions involved in the synthesis of the compounds of CHART B. CHART BG shows the general reaction scheme and the 5 reaction Steps of the compounds of CHART B. CHART BX1 shows a specific reaction scheme for a single specific compound that is generally described in CHART BG. A description of the Steps and procedures from the compounds and reactions shown in CHART BG appears below. Specific examples, with detailed procedures, follow the general steps in the example section for the compounds of CHART B. Following a description of the steps are the CHARTS BG and BX 1.

THE STEPS IN CHART BG

Step 1. $BG_0 \rightarrow BG_1$. Refer to the procedures described in CHART A to obtain the starting materials for this reaction. The compound or compounds represented by the structures shown in FIG. $BG_{0-1}$, below,

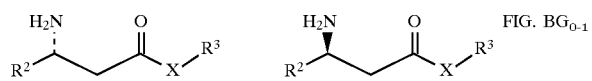

FIG. $BG_{0-1}$ where $R^2$ and $R_3$ is -($C_1$-$C_8$)alkyl, -($C_3$-$C_8$)cycloalkyl, -($C_1$-$C_8$)alkyl-(C3-C8)cycloalkyl, -($C_6$-$C_{12}$ aryl), -($C_1$-$C_8$) alkyl-($C_6$-$C_{12}$ aryl), or the aryl or alkyl is substituted with one to three of the following groups, ($C_6$-$C_{12}$ aryl),($C_1$-$C_3$) alkyl, ($C_1$-$C_3$) alkoxy, halogen, trifluoromethyl; and X is O, NH, S are reacted with a compound represented by the structure in FIG. BG-$R_1$, below,

FIG. BG-$R_1$ where $R^1$ is H, -($C_1$-$C_8$)alkyl, -($C_3$-$C_8$)cycloalkyl, -($C_1$-$C_8$) alkyl-($C_3$-$C_8$)cycloalkyl, -($C_6$-$C_{12}$ aryl), -($C_1$-$C_8$)alkyl-($C_6$-$C_{12}$ aryl), —O—($C_{1-8}$ alkyl), —O—($C_{3-8}$ cycloalkyl), —O—($C_{1-8}$ alkyl)($C_{3-8}$ cycloalkyl), —O—($C_{6-12}$ aryl), —O—($C_{1-8}$ alkyl)-aryl, or the aryl or alkyl is substituted with one to three of the following groups, ($C_6$-$C_{12}$ aryl), ($C_1$-$C_3$)alkyl, ($C_1$-$C_3$) alkoxy, halogen, trifluoromethyl, and Z is Cl, N$_3$, S-aryl,

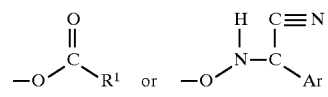

in a suitable organic solvent to yield a compound or compounds represented by the structures shown in FIG. $BG_{1-1}$, below,

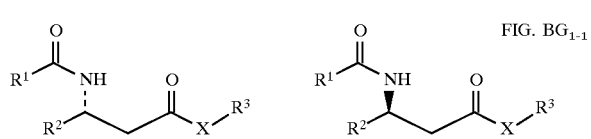

FIG. $BG_{1-1}$

Step 2. $BG_1 \rightarrow BG_2$. To a solution of the compounds represented by the structure shown in FIG. $BG_1$ in a suitable organic solvent such as tetrahydrofuran, between a temperature of −45° C.−(−78° C.), under a nitrogen atmosphere is added a compound of the following general description, FIG. GRX, below.

FIG. GRX where $R^7$ and $R^8$ are are defined independently and are -($C_1$-$C_8$)alkyl, -($C_3$-$C_8$)cycloalkyl, -($C_1$-$C_8$)alkyl-($C_6$-$C_{12}$) aryl; and M is Li, Na, or K;

The resulting dianion is then reacted with a compound represented by the structure shown in FIG. GYX, below,

FIG. GYX where $R^4$, $R^5$ and $R^6$ are defined independently and are H, -($C_1$-$C_8$)alkyl, -($C_3$-$C_8$)cycloalkyl, -($C_1$-$C_8$)alkyl-($C_3$-$C_8$) cycloalkyl, -($C_6$-$C_{12}$ aryl), -($C_1$-$C_8$)alkyl-($C_6$-$C_{12}$ aryl), or the aryl or alkyl is substituted with one to three of the following groups, -($C_6$-$C_{12}$ aryl), -($C_1$-$C_3$)alkyl, -($C_1$-$C_3$) alkoxy, halogen, trifluoromethyl; and Y is halogen, —OTs, —OMS, —OTf to obtain a compound or compounds represented by the structures shown in FIG. $BG_{2-1}$, below.

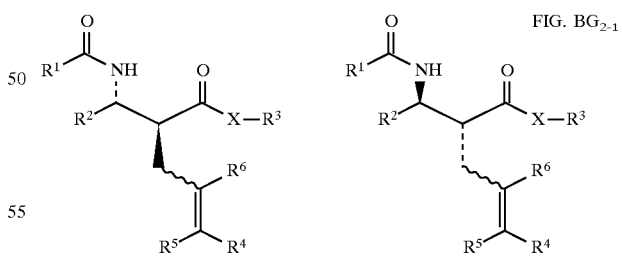

FIG. $BG_{2-1}$

Step 3. $BG_2 \rightarrow BG_3$. $BG_2$ is subjected to an established method of ozonolysis, such as bubbling $O_3$ from an ozone generator, such as a Welsbach ozonator, through the reaction mixture, followed by treatment of the intermediate carbonyl compound with $R^9$—$NH_2$ under reducing conditions, such as with sodium cyano borohydride, sodium triacetoxy borohydride or sodium borohydride, (in order of preference) at 0°–50° C., or a cool temperature to control heat, to obtain a compound or compounds represented by the structures shown in FIG. $BG_{3-1}$, below,

FIG. BG$_{3-1}$

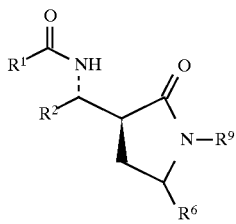

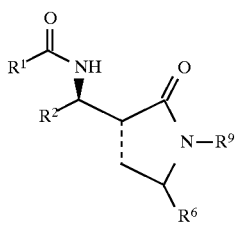

where $R^9$ is H, -($C_1$–$C_8$)alkyl, -($C_3$–$C_8$)cycloalkyl, -($C_1$–$C_8$) alkyl-($C_3$–$C_8$)cycloalkyl, -($C_6$–$C_{12}$ aryl), -($C_1$–$C_8$)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl.

Step 4. BG$_3$→BG$_4$. BG$_3$ is reduced by LAH, DIBAL, Borane, etc. to obtain the compound or compounds represented by the structures shown in FIG. BG$_{4-1}$, below,

FIG. BG$_{4-1}$

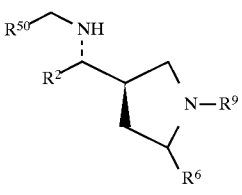

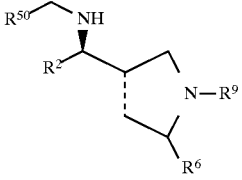

where $R^{50}$ is H, -($C_1$–$C_8$)alkyl, -($C_3$–$C_8$)cycloalkyl, -($C_1$–$C_8$)alkyl-($C_3$–$C_8$)cycloalkyl, -($C_6$–$C_{12}$ aryl), -($C_1$–$C_8$) alkyl-($C_6$–$C_{12}$ aryl), or the aryl or alkyl is substituted with one to three of the following groups, ($C_6$–$C_{12}$ aryl), ($C_1$–$C_3$) alkyl, ($C_1$–$C_3$) alkoxy, halogen, trifluoromethyl. When $R^1$ is —O—($C_{1-8}$ alkyl), —O—($C_{3-8}$ cycloalkyl), —O—($C_{1-8}$ alkyl)($C_{3-8}$ cycloalkyl), —O—($C_{6-12}$ aryl), —O—($C_{1-8}$ alkyl)-aryl, then reduction with LAH, DIBAL or Borane will always produce $R^{50}$ is H.

Step 5. BG$_4$→BG$_5$. When it is desired to make $R^9$ a protective group, where for example an alkylaryl is connected to the nitrogen atom with one carbon atom between the nitrogen and the aryl, that is where aryl is bound to the first carbon in the alkyl side chain, then this deprotection step 5 may be used. For example, if $R^9$ is benzyl, FIG. BG$_4$ could be hydrogenolytically cleaved with 10 percent palladium hydroxide on charcoal, H$_2$; to obtain a compound represented by the structure shown in FIG. BG$_5$ below.

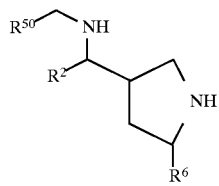

FIG. BG$_5$

Depending upon the starting materials used, compounds represented by the structure shown by FIG. BG$_5$ may have one of either of the two steriochemical arrangements shown by the structures below, FIG. BG$_{5-1}$,

FIG. BG$_{5-1}$ or, if the starting materials are a racemic mixture, the reaction may produce a 1:1 ratio of the combination of products shown in FIG. BG$_{5-1}$, i.e. a racemic mixture. When $R^9$ is not a protective group, as described above, step 5 cannot be performed.

EXAMPLES FROM CHART B

The specific procedures and examples described below, shown in CHART BX1 (t-butyl ester shown in chart, ethyl ester used below) are to be construed as merely illustrative, and do not impose limitations upon the general reaction schemes in any manner whatsoever. Those skilled in the art will promptly recognize appropriate variations from the procedures both as to reactants as well as to reaction conditions and techniques. The actual NMR data provided below each step was obtained from the racemic mixture. The specific enantiomer shown in the steps below by using the appropriate starting materials. Although the ethyl ester is shown in the steps below, the t-butyl ester could also be used as is shown in CHART BX1.

Step 1. Preparation of Ethyl (S)-3-carboxybenzylaminobutyrate.

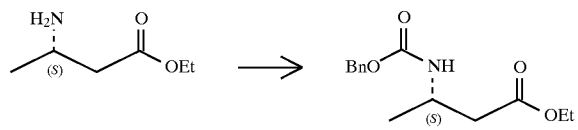

Cool a a solution of ethyl 3-aminobutyrate (20 g, 153 mmol.) in pyridine (55 ml), to 0° C. and add benzyl chloroformate (32.6 ml, 39.0 g, 229 mmol) over a 45 minute period. Stir the resulting reaction mixture at room temperature under N$_2$ for 20 hours. Partition the reaction mixture between ethyl ether and 2% (aq.) H$_2$SO$_4$. Separate the layers. The organic layer is washed with 2% (aq.) H$_2$SO$_4$, 5% (aq.) NaHCO$_3$ and brine. The organic layer was dried over MgSO$_4$, filtered and concentrated to yield ethyl 3-carboxybenzylamino butyrate: ¹H NMR (300 MHz, CDCl₃) δ1.24 (d, J is 6.7 Hz, 3H), 1.25 (t, J is 7.1 Hz, 3H), 2.52 (d, J is 5.6 Hz, 2H), 4.12 (m, 1H), 4.14 (q, J is 7.1 Hz, 2H), 5.09 (s, 2H), 5.24 (broad s, 1H), 7.31–7.38 (m, 5H).

Step 2. Preparation of Ethyl (S,S)-2-(1'-(carboxybenzylamino)ethyl)-4-pentenoate.

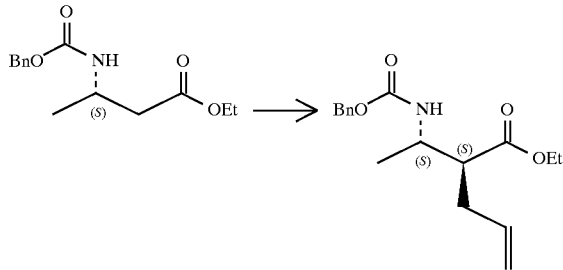

To a solution of i-Pr₂NH (2.93 ml, 20.88 mmol) in tetrahydrofuran (20 ml) at −30° C. and under a nitrogen atmosphere add 1.6M n-BuLi (11.5 ml, 18.37 mmol). The resulting solution of LDA was allowed to warm to −10° C. over 50 min. and was then cooled to −55° C. Ethyl (S)-3-carboxybenzylaminobutyrate (2.0 ml, 8.35 mmol), in solution in tetrahydrofuran (20 ml) at room temperature, is added during a 5 minute period to the −55° C. solution of LDA. The temperature may rise to −48° C. during this addition. The reaction is cooled to −56° C. and tetrahydrofuran (20 ml) is added over 3 minutes to the reaction mixture. After 30 minutes allylbromide (2.89 ml, 33.40 mmol) is added during a 3 minute period to the −45° C. reaction mixture. The reaction mixture is maintained at −45° C. for 20 minutes and is then allowed to warm to room temperature during a 12 hour period. The reaction mixture is combined with saturated aqueous NH₄Cl (100 mls) and is extracted with CH₂Cl₂ (5×100 mls). The combined organic extracts are dried over MgSO₄, filtered and concentrated by rotary evaporation. The resulting crude oil is chromatographed (SiO₂, 5:1 Hx : EtOAc) to yield ethyl (S,S)-2-[1'-(carboxybenzylamino)ethyl]-4pentenoate: ¹H NMR (300 MHz, CDCl₃) δ 1.17 (d, J is 6.8 Hz, 3H), 1.25 (t, J is 7.1 Hz, 3H), 2.29 (ddd, J is 14.0, 7.0, 7.0 Hz, 1H), 2.40 (ddd, J is 14.0 7.0 Hz, 1H), 2.53 (m, 1H), 3.97 (m, 1H), 4.14 (q, J is 7.1 Hz, 2H), 5.03 (d, J is 10 Hz, 1H), 5.06 (d, J is 16 Hz, 1H), 5.09 (s, 2H), 5.57 (broad d, J is 9 Hz, 1H), 5.74 (ddd, J is 16, 10, 7 Hz, 1H), 7.30–7.37 (m, 5H).

Step 3. Preparation of (S,S)-1-benzyl-2-oxo-3-(1'-(carboxybenzylamino)ethyl)pyrrolidin.

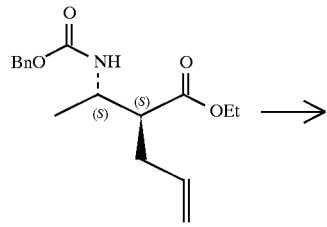

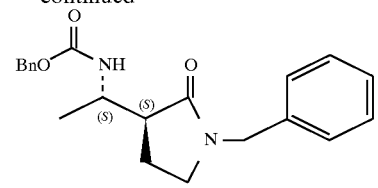

Ethyl (S,S)-2-[1'-(carboxybenzylamino)ethyl]-4-pentenoate (2.19 g, 7.18 mmol) is dissolved in MeOH (50 ml) and the resulting solution cooled to −78° C. O₃, from a Welsbach ozonator set at the standard settings, is bubbled through the reaction mixture until starting material can no longer be detected by thin-layer chromatography (2:1 hexane: EtOAc). Dimethyl sulfide (5 ml) is added to the reaction mixture which is allowed to warm to room temperature and is then concentrated by rotary evaporation. The crude aldehyde is dissolved in methanol (25 ml) and tetrahydrofuran (25 ml) and the resulting solution is cooled to 0° C. under a nitrogen atmosphere. Benzyl amine (4.06 ml, 37.15 mmol) followed by acetic acid (4.68 ml, 81.73 mmol) is added to the reaction mixture which is then stirred at 0° C. for 12 min. NaCNBH₃ (0.95 g, 14.86 mmol) is added to the reaction mixture which is allowed to warm to room temperature and continuously stirred for a 24 hour period. The reaction mixture is adjusted to pH 9 with 1N NaOH and the resulting mixture is partitioned between EtOAc and water. The layers are separated and the aqueous layer is extracted with EtOAc. The combined organic layers are dried over MgSO₄, filtered and then concentrated by rotary evaporation. The crude product is purified by chromatography (1:1 hexane : EtOAc) to give (S,S)-1-benzyl-2-oxo-3-[1'-(carboxybenzylamino) ethyl] pyrrolidine: ¹H NMR (300 MHz, CDCl₃) δ 1.30 (d, J is 7 Hz, 3H), 1.77 (ddd, J is 16, 12, 9 Hz, 1H), 2.04 (m, 1H), 2.59 (ddd, J is 9, 9, 4 Hz, 1H), 3.04–3.09 (m, 2H), 3.95 (m, 1H), 4.34 (s, 2H), 5.01 (s, 2H), 5.11 (broad s, 1H), 7.10–7.28 (m, 10H), Step 4. Preparation of (R,S)-1-benzyl-3-[1'-(methylamino)ethyl]pyrrolidine.

(S,S)-1-benzyl-2-oxo-3-[1'-(carboxybenzylamino)ethyl] pyrrolidine (0.51 g, 1.44 mmol) is dissolved in tetrahydrofuran (20 ml) under a N₂ atmosphere. LAH (0.32 g, 8.43 mmol) is added and the reaction mixture is refluxed for 12 hours. The reaction mixture is cooled to 0° C., diluted with Et₂O and quenched with 15% aqueous NaOH. The resulting mixture is filtered through a celite pad which is then washed carefully with Et₂O. The filtrate is washed with 15% aqueous NaOH and the aqueous layer extracted with Et₂O. The combined Et₂O layers are dried over MgSO₄, filtered and concentrated under a stream of N₂ to give crude (R,S)-1- benzyl-3-[1'-(methylamino)ethyl]pyrrolidine: $^1$H NMR (300 MHz, CDCl$_3$) δ 1.04 (d, J is 6 Hz, 3H), 1.52 (m, 1H), 1.93 (m, 1H), 2.17 (m, 1H), 2.25 (dd, J is 16, 8 Hz, 1H), 2.37 (s, 3H), 2.33–2.49 (m, 2H), 2.56 (dd, J is 15, 8 Hz, 1H), 2.77 (dd, J is 8, 8 Hz, 1H), 3.58 (d, J is 12.8 Hz, 1H), 3.60 (d, J is 12.8 Hz, 1H), 7.23–7.36 (m, 5H). This crude material is suitable for use in Step 5.

Step 5. Preparation of (R,S)-3-[1'-(methylamino)ethyl] pyrrolidine.

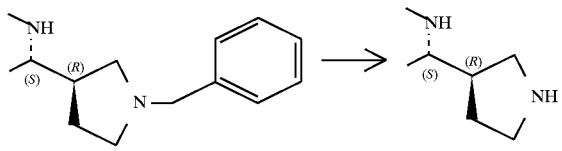

(R,S)-1-benzyl-3-[1'-(methylamino)ethyl]pyrrolidine (0.51 g of crude product) is dissolved in MeOH (10 ml) under a N$_2$ atmosphere, Pearlman's catalyst and ammonium formate (0.89 g, 14.11 mmol) are then added. The reaction mixture is refluxed for 12 hours. The reaction mixture is then diluted with CH$_2$Cl$_2$:MeOH (1:1) and filtered through a celite pad. The filtrate is washed with 15% aqueous NaOH:brine (1:1) and the aqueous layer is back extracted with CH$_2$Cl$_2$ (2×). The combined organic layers are dried over MgSO$_4$, filtered and concentrated under a stream of N$_2$ to give crude (R,S)-3-[1'-(methylamino)ethyl]pyrrolidine: $^1$H NMR (300 MHz, CDCl$_3$) δ 1.05 (d, J is 6.3 Hz, 3H), 1.43 (ddd, J is 17, 12, 9 Hz, 1H), 1.87 (m, 1H), 2.02 (dd, J is 16, 8 Hz, 1H), 2.38 (s, 3H), 2.41 (m, 1H), 2.61 (broad s, 2H), 2.65 (dd, J is 11, 8 Hz, 1H), 2.91–3.00 (m, 2H), 3.13 (dd, J is 11, 8 Hz, 1H). This material is suitable for use in various reactions including but not limited to the synthesis of quinolones.

THE REACTIONS AND COMPOUNDS OF CHART C-G

The procedures below refer to CHART C-G.

Step 1(b) Formation of CG$_{1(b)}$. An appropriate optically active amine, such as a compound represented by the structures shown in FIG. CG-R$_1$, below,

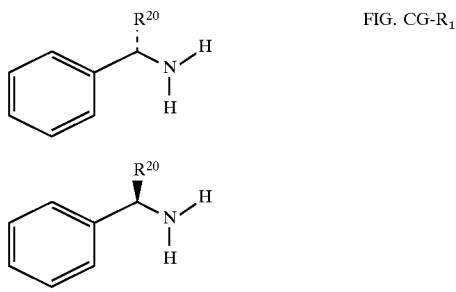

where R$^{20}$ is -(C$_1$–C$_8$)alkyl, -(C$_3$–C$_8$)cycloalkyl, -(C$_1$–C$_8$) alkyl-(C$_3$–C$_8$)cycloalkyl, -(C$_6$–C$_{12}$ aryl), -(C$_1$–C8)alkyl-(C$_6$–C$_{12}$ aryl), or the aryl or alkyl is substituted with one to three of the following groups, -(C$_6$–C$_{12}$ aryl), -(C$_1$–C$_3$)alkyl, -(C$_1$–C$_3$) alkoxy, halogen, trifluoromethyl, is condensed with a carbonyl compound, such as one represented by the structure shown in FIG. CG-R$_2$ below,

where R$^{21}$ and R$^{22}$ are defined independently and are H, -(C$_1$–C$_8$)alkyl, -(C$_3$–C$_8$)cycloalkyl, -(C$_1$–c$_8$)alkyl-(C$_3$–C$_8$) cycloalkyl, -(C$_6$–C$_{12}$ aryl), -(C$_1$–C$_8$)alkyl-(C$_6$–C$_{12}$ aryl), or the aryl or alkyl is substituted with one to three of the following groups, -(C$_6$–C$_{12}$ aryl), -(C$_1$–C$_3$)alkyl, -(C$_1$–C$_3$) alkoxy, halogen, trifluoromethyl; under reducing conditions using NaBH$_4$ or a similar suitable boron hydride reducing agent in a suitable solvent such as THF to obtain compounds represented by the structures shown in FIG. CG$_{1(b)}$ below,

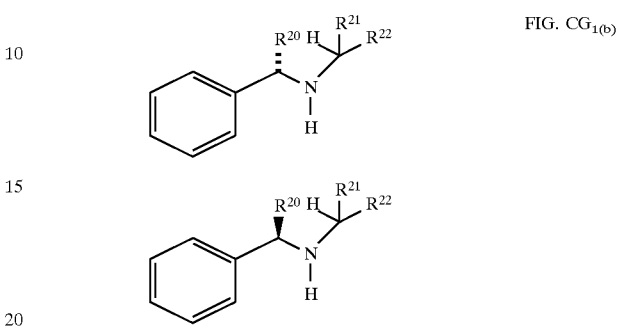

Step 2 CG$_{1(a)}$+CG$_{1(b)}$→CG$_2$. A compound represented by the structures shown in CG$_{1(a)}$, below,

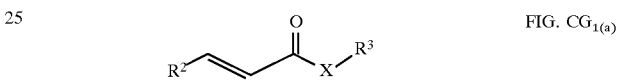

where, R$^2$ and R$^3$ are independently, lower alkyl, alkylaryl, or optionally substituted aryl, and and where X is O, NH, S; undergoes a Michael Addition reaction, between 0° and -100° C. temperature, but preferably at -70 to -80° C., with a compound represented by the deprotonated form of the structures shown in FIG. CG$_{1(b)}$. Deprotonation is performed between 0° and -100° C., but preferably between -30° to -50° C., with an appropriate base such as n-BuLi, to produce compounds, after coupling, represented by the structures shown in FIG. CG$_2$ below,

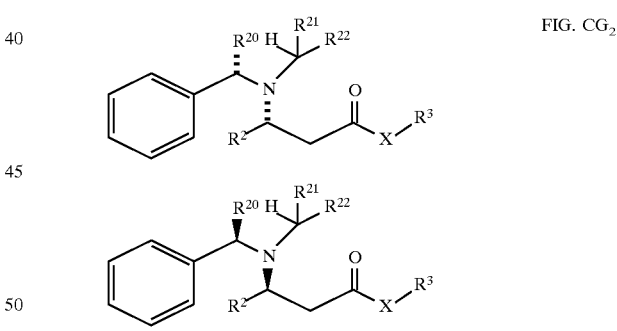

Step 3 CG$_2$→CG$_3$. Since the amine nitrogen of structures CG$_2$ has a benzyl substituent, this nitrogen may be deprotected. The carbon nitrogen bonds are hydrogenolytically cleaved with an appropriate reducing agent such as Pearlrnan's catalyst, 20 percent palladium hydroxide on charcoal, in an appropriate solvent, such as EtOH, to obtain the compounds represented by the structures shown in FIG. CG$_3$.

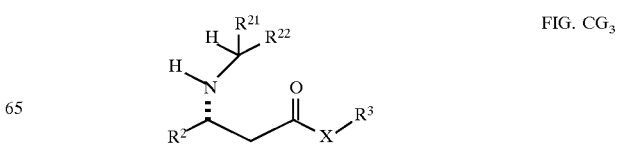

-continued

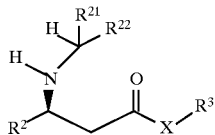

Compounds represented by the structures shown in FIG. $CG_3$ are then used as starting materials for the reactions of CHARTS D.

THE REACTIONS AND COMPOUNDS OF CHART D-G.

The procedures below refer to CHART D-G.

Step 1. $DG_0 \rightarrow DG_1$. Refer to the procedures described in CHART C to obtain the starting materials for this reaction. The compounds represented by the structures in FIG. $DG_0$, below,

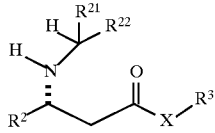

FIG. $DG_0$

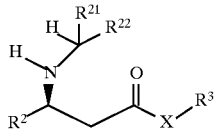

(Where $R^{21}$ and $R^{22}$ are defined independently and are H, -($C_1$–$C_8$)alkyl, -($C_3$–$C_8$)cycloalkyl, -($C_1$–$C_8$)alkyl-($C_3$–$C_8$) cycloalkyl, -($C_6$–$C_{12}$ aryl), -($C_1$–$C_8$)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl. Where $R^2$ and $R^3$ are defined independently and are lower alkyl, alkylaryl, or optionally substituted aryl) and where X is O, NH, S; are dissolved in a suitable organic solvent such as tetrahydrofuran, and then added, between a temperature of –50° C. and 0° C., preferably around –30° or –40° C., in a nitrogen atmosphere, to a solution of a compound of the description in FIG. GRX, dissolved in a suitable organic solvent.

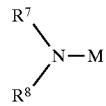

FIG. GRX (Where $R^7$ and $R^8$ are defined independently and are -($C_1$–$C_8$)alkyl, -($C_3$–$C_8$)cycloalkyl, -($C_1$–$C_8$)alkyl-($C_6$–$C_{12}$) aryl; where M is Li, Na, or K) Note that the compounds represented by the FIG. GRX contain R groups, $R^7$ and $R^8$, that are not incorporated into the desired compounds, FIG. GRX represents a compound that only acts as a base. This use of the compounds of FIG. GRX applies to all the reactions of this invention. The resulting anion or dianion is then reacted with a compound represented by the structure shown in FIG. GYX, below,

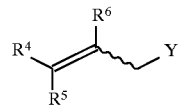

FIG. GYX (Where $R^4$, $R^5$, and $R^6$ are independent and are H, alkyl, alkylaryl, or optionally substituted aryl, and where Y is halogen, —OTs, —OMs, or —OTf.) to obtain a compound represented by the structures shown in FIG. $DG_1$, below.

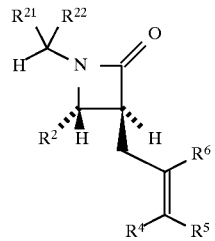

FIG. $DG_1$

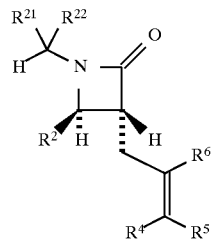

Step 2. $DG_1 \rightarrow DG_2$. $DG_1$ is subjected to an established method of ozonolysis, such as bubbling $O_3$ from an ozone generator, such as a Welsbach ozonator, through the reaction mixture in an appropriate solvent, such as water or methanol, followed by reduction of the intermediate ozonide with an appropriate boron hydride reducing agent such as $NaBH_4$ or $LiBH_4$ to obtain a compound represented by the structures shown in FIG. $DG_2$, below.

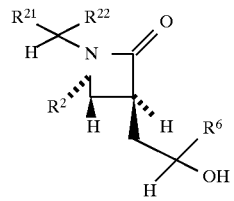

FIG. $DG_2$

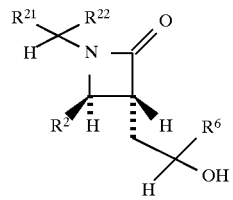

Step 3. $DG_2 \rightarrow DG_3$. $DG_2$ is treated with an appropriate amine base, such as triethylamine, and an activating agent, such as methanesulfonyl chloride in a solvent such as tetrahydrofuran or toluene to obtain a compound represented by the structures shown in FIG. $DG_3$, where Ms is mesylate, below.

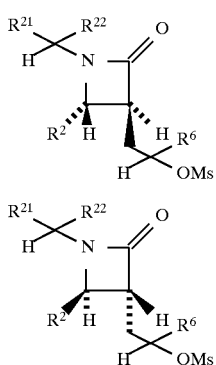

FIG. DG₃

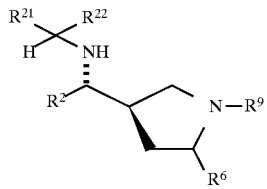

FIG. DG₆

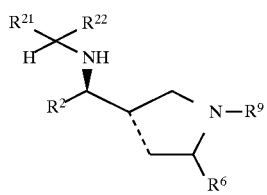

Step 4. DG₃→DG4. DG₃ is treated in an appropriate solvent such as toluene or THF with an amine represented by the structure shown in FIG. DG-R₁ below,

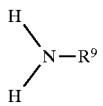

FIG. DG-R₁

(where $R^9$ is defined previously) to obtain a compound represented by the structures shown in FIG. DG₄ below.

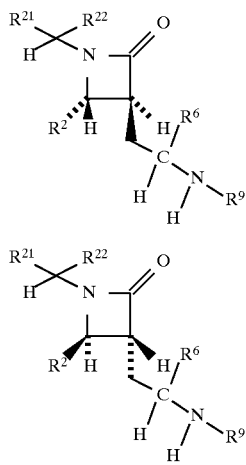

FIG. DG₄

Step 7. DG₆→DG₇. When $R^9$ is a $C_1$–$C_6$ alkyl the reaction stops, and if R₉ is an alkylaryl that is connected to the nitrogen atom with more than one carbon atom between the nitrogen and aryl, the reaction will also stop. When it is desired to make $R^9$ a protective group, where for example an alkylaryl is connected to the nitrogen atom with one carbon atom between the nitrogen and the aryl, that is where the aryl is bound to the first carbon atom in the alkyl side chain, then this deprotection step 7 may be used. For example if $R^9$ is benzyl, FIG. DG₆ could be hydrogenolytically cleaved with 20 percent palladium hydroxide on charcoal; to obtain a compound represented by the structures shown in FIG. DG₇ below,

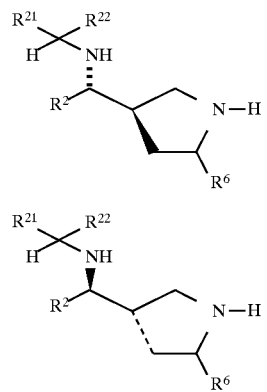

FIG. DG₇

Step 5. DG₄→DG₅. In the same reaction vessel as step 4, above, DG₄ thermally isomerizes to give a compound represented by the structures shown in FIG. DG₅ below.

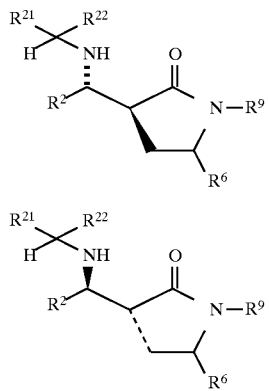

FIG. DG₅

Depending upon the starting materials used, compounds represented by the structures on the left side of the figures or the right side of the figures or, if the starting materials are a racemic mixture, the reaction may produce a 1:1 ratio of compounds represented on both sides of the FIG. DG₇, i.e. a racemic mixture.

EXAMPLES OF COMPOUNDS FROM CHART D-G.

Using appropriate starting materials using the procedures shown in CHART D, can be used to make the following compounds:

3-(1'-(S)-benzylamino)ethyl)pyrrolidine and 3-(1'-(S)-methylamino)ethyl)pyrrolidine.

3-(1'-(S)-benzylamino)ethyl)pyrrolidine and 3-(1'-(S)-ethylamino)ethyl)pyrrolidine.

THE REACTIONS AND COMPOUNDS OF CHART E-G

Step 6. DG₅→DG₆. DG₅ is treated with a suitable reducing agent such as LiAlH₄, DIBAL or Borane in a suitable The procedures below, which are the more preferred procedures, refer to CHART E-G.

Step 1(a) Formation of $EG_{1(b')}$. A compound represented by the structures shown in FIG. EG-R$_1$, below,

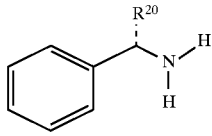

FIG. EG-R$_1$

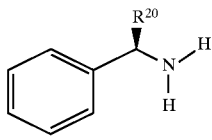

(where $R^{20}$ is -($C_1$-$C_8$)alkyl, -($C_3$-$C_8$)cycloalkyl, -($C_1$-$C_8$)alkyl-($C_3$-$C_8$)cycloalkyl, -($C_6$-$C_{12}$ aryl), -($C_1$-$C_8$)alkyl-($C_6$-$C_{12}$ aryl), or the aryl or alkyl is substituted with one to three of the following groups, -($C_6$-$C_{12}$ aryl), -($C_1$-$C_3$)alkyl, -($C_1$-$C_3$) alkoxy, halogen, trifluoromethyl,), is condensed with a compound represented by the structure shown in FIG. EG-R$_2$ below,

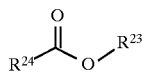

FIG. EG-R$_2$ (where $R^{23}$ is -($C_1$-$C_8$)alkyl, -($C_3$-$C_8$)cycloalkyl, -($C_1$-$C_8$)alkyl-($C_3$-$C_8$)cycloalkyl, -($C_6$-$C_{12}$ aryl), -($C_1$-$C_8$)alkyl-($C_6$-$C_{12}$ aryl), or the aryl or alkyl is substituted with one to three of the following groups, -($C_6$-$C_{12}$ aryl), -($C_1$-$C_3$)alkyl, -($C_1$-$C_3$) alkoxy, halogen, trifluoromethyl;

where $R^{24}$ is H, -($C_1$-$C_8$)alkyl, -($C_3$-$C_8$)cycloalkyl, -($C_1$-$C_8$)alkyl-($C_3$-$C_8$)cycloalkyl, -($C_6$-$C_{12}$ aryl), -($C_1$-$C_8$) alkyl-($C_6$-$C_{12}$ aryl), or the aryl or alkyl is substituted with one to three of the following groups, -($C_6$-$C_{12}$ aryl), -($C_1$-$C_3$)alkyl, -($C_1$-$C_3$) alkoxy, halogen, trifluoromethyl; to obtain a compound represented by the structures shown in FIG. $EG_{1(b')}$ below,

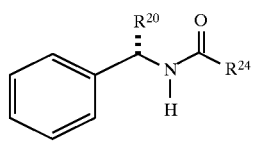

FIG. $EG_{1(b')}$

Step 1(b) $EG_{1(b')} \to EG_{1(b)}$. $EG_{1(b')}$ is treated with an appropriate reducing agent such as LiAlH$_4$, DIBAL or Borane in a suitable solvent such as THF to obtain compounds represented by the structures shown in FIG. $EG_{1(b)}$, below.

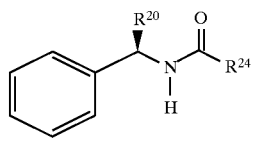

FIG. $EG_{1(b)}$

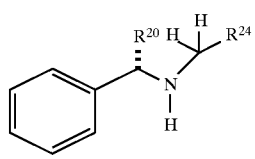

Step 2 $EG_{1(a)} + EG_{1(b)} \to EG_2$ A compound represented by the structures shown in $EG_{1(a)}$, below,

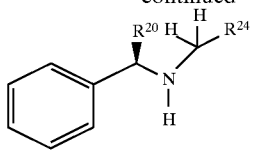

FIG. $EG_{1(a)}$ (where $R^2$ are $R^3$ are independently, lower alkyl, arlkylaryl, or optionally substituted aryl), where X is O, NH, S; undergoes a Michael Addition reaction with a compound represented by the deprotonated form of the structures shown in FIG. $EG_{1(b)}$. Deprotonation is carried out with an appropriate base such as n-BuLi, to produce compounds, after coupling, represented by the structures shown in FIG. $EG_2$, below.

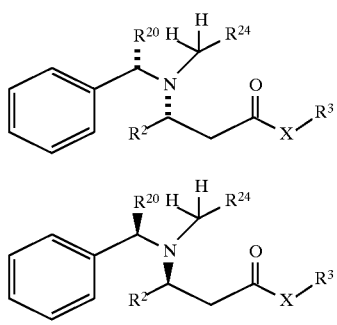

FIG. $EG_2$

Step 3 $EG_2 \to EG_3$. Since the amine nitrogen of structures $EG_2$ has a benzyl substituent, this nitrogen may be deprotected. The carbon nitrogen bonds are hydrogenolytically cleaved with an appropriate reducing agent such as Pearlman's catalyst, 20 percent palladium hydroxide on charcoal, in an appropriate solvent, such as EtOH, to obtain the compounds represented by the structures shown in FIG. $EG_3$.

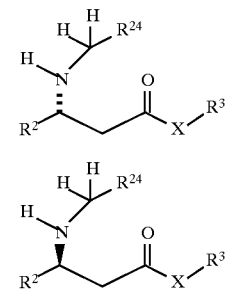

FIG. $EG_3$

The compounds represented by the structures shown in FIG. $EG_3$ are used as the starting materials for the reactions of CHARTS F, F-G & F-X.

THE REACTIONS AND COMPOUNDS OF CHART F-G

The procedures below refer to CHART FG.

Step 1 $FG_0 \to FG_1$. Refer to the procedures described in CHART E to obtain the starting materials for this reaction.

The compounds represented by the structures shown in FIG. $FG_0$, below,

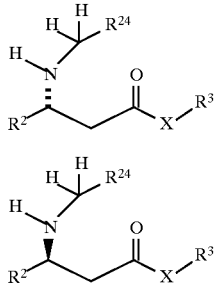

FIG. $FG_0$ (Where $R^{24}$ is H, -($C_1$–$C_8$)alkyl, -($C_3$–$C_8$)cycloalkyl, -($C_1$–$C_8$)alkyl-($C_3$–$C_8$)cycloalkyl, -($C_6$–$C_{12}$ aryl), -($C_1$–$C_8$) alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$)alkoxy, halogen, trifluoromethyl;, and where X is O, NH, or S; and where $R^2$ and $R^3$ are defined independently and are lower alkyl, alkylaryl, or optionally substituted aryl) are dissolved in a suitable organic solvent such as tetrahydrofuran, and added, between a temperature of –50° C. and 0° C., in an inert atmosphere or an atmosphere without water, preferably about –30° or –40° C., in a nitrogen atmosphere; to a solution of a compound represented by the structures shown in FIG. FG-$R_1$, below.

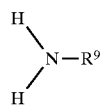

FIG. FG-$R_1$ (Where $R^9$ is H, -($C_1$–$C_8$)alkyl, -($C_3$–$C_8$)cycloalkyl, -($C_1$-$C_8$)alkyl-($C_3$–$C_8$)cycloalkyl, -$C_6$–$C_{12}$ aryl), -($C_1$–$C_8$)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl). The resulting anion or dianion is then reacted with a compound represented by the structures shown in FIG. GYX, below,

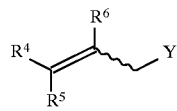

FIG. GYX (Where $R^4$, $R^5$, and $R^6$ are independent and are H, alkyl, alkylaryl, or optionally substituted aryl, and where Y is halogen, —OTs, —OMs, or -OTf) to obtain a compound represented by the structures shown in FIG. $FG_1$, below,

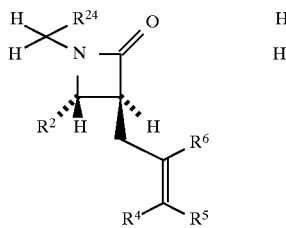

FIG. $FG_1$

Step 2. $FG_1 \rightarrow FG_2$. $FG_1$ is subjected to an established method of ozonolysis, such as bubbling $O_3$ from an ozone generator, such as a Welsbach ozonator, through the reaction mixture in an appropriate solvent such as water or methanol, followed by treatment of the intermediate ozonide with an appropriate boron hydride reducing agent such as $NaBH_4$ or $LiBH_4$ to obtain a compound represented by the structures shown in FIG. $FG_2$, below.

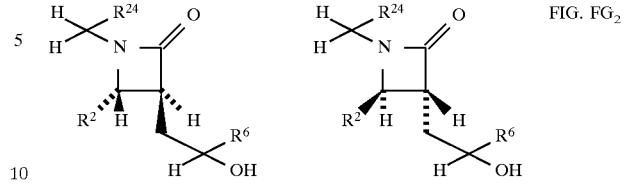

FIG. $FG_2$

Step 3. $FG_2 \rightarrow FG_3$. $FG_2$ is treated with an appropriate amine base, such as triethylamine, and methanesulfonyl chloride in a solvent such as tetrahydrofuran or toluene to obtain a compound represented by the structures shown in FIG. $FG_3$, where Ms is mesylate, below.

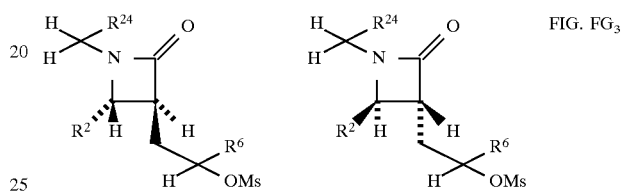

FIG. $FG_3$

Step 4. $FG_3 \rightarrow FG_4$. $FG_3$ is treated in an appropriate solvent such as toluene or THF with an amine represented by the structure shown in FIG. FG-$R_1$ below,

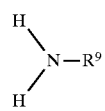

FIG. FG-$R_1$ (where $R^9$ is defined earlier) to obtain a compound represented by the structures shown in FIG. $FG_4$ below,

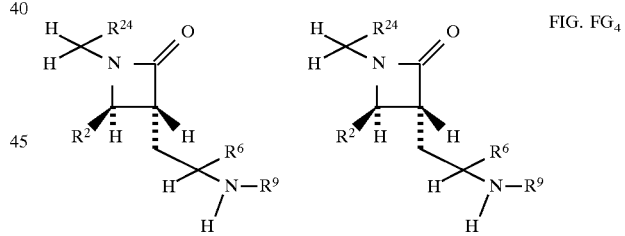

FIG. $FG_4$

Step 5. $FG_4 \rightarrow FG_5$. In the same reaction vessel as step 4 above, $FG_4$ thermally isomerizes to give a compound represented by the structures shown in FIG. $FG_5$ below,

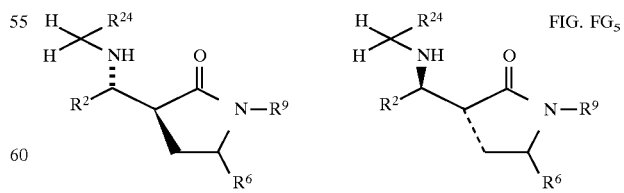

FIG. $FG_5$

Step 6. $FG_5 \rightarrow FG_6$. $FG_5$ is treated with a suitable reducing agent such as $LiAlH_4$, DIBAL or Borane in a suitable solvent such as THF to obtain a compound represented by the structures shown in FIG. $FG_6$ below,

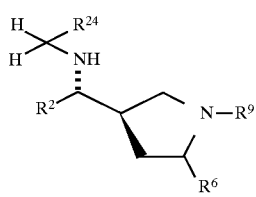 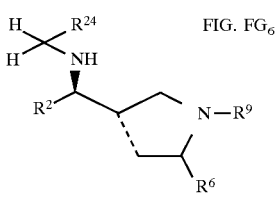

FIG. FG₆

Step 7. FG₆→FG₇. When $R^9$ is a $C_1$–$C_6$ alkyl the reaction stops, and if $R_9$ is an alkylaryl that is connected to the nitrogen atom with more than one carbon atom between the nitrogen and aryl, the reaction will also stop. When it is desired to make $R^9$ a protective group, where for example an alkylaryl is connected to the nitrogen atom with one carbon atom between the nitrogen and the aryl, that is where the aryl is bound to the first carbon in the alkyl side chain, then this deprotection step 7 may be used. For example if $R^9$ is benzyl, FIG. FG₆ could be hydrogenolytically cleaved with 20 percent palladium hydroxide on charcoal; to obtain a compound represented by the structures shown in FIG. FG₇ below,

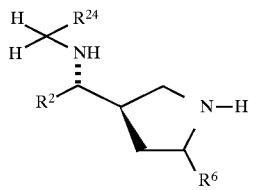 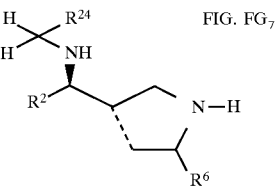

FIG. FG₇

Depending upon the starting materials used, compounds represented by the structures on the left side of the figures or the right side of the figures or, if the starting materials are a racemic mixture, the reaction may produce a 1:1 ratio of compounds represented on both sides of the FIG. FG₇, i.e. a racemic mixture.

EXAMPLES OF COMPOUNDS FROM CHART E–CHART EX1

The specific procedures and examples described below, shown in CHART EX1 are to be construed as merely illustrative of the procedures described above, and do not impose limitation upon the general reaction schemes in any manner whatsoever. Those skilled in the art will promptly recognize appropriate variations from the procedures both as to reactants as well as to reaction conditions and techniques.

Step 1(a) of CHART EX1. Synthesis of N-Formyl-N-(S)-1-phenylethylamine, $EX1_{1(b')}$. Add (S)-(−)-phenylethylamine (940 g) and ethyl formate (1.83 kg) to a 5000 ml. flask. Heat the solution to reflux and stir overnight. Remove the excess ethyl formate in vacuo leaving 1.15 kg of N-formyl-(S)-1-phenylethylamnine. $^{13}$CNMR (CDCl₃, ppm δ) 21.80, 47.61, 126.11, 127.42, 128.66, 142.73, 160.60.

STEP 1(b) of CHART EX1. Synthesis of N-Methyl-N-(S)-1-phenylethylamine, $EX_{1(b')}$. Add powdered LiAlH₄ (50 g) and THF (500 mL) to a 3000 ml flask. Then add a solution of N-formyl-N-(S)-1-phenylethylamine ($EX1_{1(b')}$, 100 g) in THF (500 mL) dropwise into the LiAlH₄ solution. Heat the solution to reflux and stir 5 hours. After reflux, cool the solution to 5° C. and slowly quench the reaction with 10% NaOH (500 mL), then extract the product with MTBE (1×2 L). Remove the solvent in vacuo, and purify the product by distillation to yield 70 g (78%) of N-methyl-N-(S)-1-phenylethylamine. $^{13}$CNMR (CDCl₃, ppm δ) 24.15, 34.76, 60.49, 126.84, 127.14, 128.65, 145.64.

Step 2 of CHART EX1. Synthesis of 3-(N-Methyl-N-(S)-1'-phenylethylamino)butyric acid, 2-methylpropyl ester, $EX1_2$. Add N-methyl-N-(S)-1-phenylethylamine ($EX1_{1b}$, 390.0 g, 2.88 mol, 1.1 eq) and THF (14 L) to a 22 L flask. Cool this solution to −5° C. and add n-buLi (1.80 L, 2,88 mol,) over a period of 30 min. maintaining the internal reaction temperature below 0° C. The solution is stirred at 0° C. for 30 min. and then cooled to −78° C. A pre-cooled, to −40° C., solution of isobutyl crotonate (372 g) in THF (3.0 L) is added at a rate such that the internal reaction temperature does not exceed −70° C. After the addition is complete, the reaction is stirred at −75° C. for 30 min. The reaction is quenched with saturated NH₄Cl until the pH is between about 9 to 11. The organic phase is separated and the solvent is removed in vacuo. The product is redissolved in EtOAc (1.5 L) and the resulting solution is filtered. The EtOAc is distilled off and MeOH (1.0 L) and 37% HCl (210 mL) are added. MTBE (5 L) is added to crystallize the amine hydrochloride salt of the 2-methylpropyl ester of 3-(N-methyl-N-(S)-1'-phenylethylamino)butyric acid. The crystalline amine hydrochloride salt is dissolved in CH₂Cl₂ (2.5 L) and water (1.0 L) is added. A 10% NaOH solution is used to adjust the pH to between about 9 to 11. The organic layer is separated and the solvent is removed in vacuo to yield 290 g (65%) of 3-(N-methyl-N-(S)-1'-phenylethylamino)butyric acid, 2-methylpropyl ester. $^{13}$CNMR (CDCl₃, ppm δ) 14.70, 19.39, 21.97, 27.95, 32.31, 39.25, 51.43, 62.36, 70.70, 126.91, 127.40, 128.47, 146.45, 173.06.

Step 3 of CHART EX1. Synthesis of 3-(N-Methylamino) butyric acid, 2-methylpropyl ester, $EX1_3$. Add 20 wt % Pd(OH)₂ on carbon (5.0 g) to a 4 L Parr shaker, followed by ethanol and 3-(N-methyl-N-(S)-1'-phenylethylamino) butyric acid, 2-methylpropyl ester ($EX1_2$) . Pressurize the Parr shaker to 70 atm with H₂. No further H₂ uptake after 1.5 hours indicates the reaction is complete. When the reaction is complete, filter off the catalyst and remove the solvent in vacuo to yield 65 g (100%) of 3-(N-methylamino)butyric acid, 2-methylpropyl ester. $^{13}$CNMR (CDCl₃, ppm δ) 16.56, 19.05, 27.60, 30.32, 37.47, 52.23, 71.42, 169.81.

EXAMPLES OF COMPOUNDS FROM CHART F–CHART FX1

The specific procedures and examples described below, shown in CHART FX1 are to be construed as merely illustrative of the procedures described above, and do not impose limitation upon the general reaction schemes in any manner whatsoever. Those skilled in the art will promptly recognize appropriate variations from the procedures both as to reactants as well as to reaction conditions and techniques.

Step 1 of CHART FX1. Synthesis of 3-[(S)-2'-propenyl] -2-(S)-methyl-N-methylazetidinone, $FX1_1$. Add diisopropylamine (83.4 g) and THF (1.5 L) to a 5 ml flask. This solution is cooled to −10° C., and 1.6M n-BuLi (515 mL, 825 mmol) is added at a rate such that the internal temperature does not exceed 0° C. After 30 min, cool the solution to −40° C., and add the 2-methylpropyl ester of 3-(N-methylamino)butyric acid ($EX1_3$, 65 g). After 30 minutes stirring add the allyl bromide (91 g) and stir an additional 30 minutes, then quench with saturated NH₄Cl (350 mL). The organic layer is separated, and the solvent is removed in vacuo. Purification by silica gel chromatography (33% EtOAc:heptane) yields 42 g (80%) of 3-[(S)-2'-propenyl]-2-(S)-methyl-N-methylazetidinone. $^{13}$CNMR (CDCl₃, ppm δ) 17.15, 25.80, 32.16, 54.46, 56.44, 116.57, 134.60, 169.12.

Step 2 of CHART FX1. Synthesis of 3-[(S)-2'-hydroxyethyl]-2-(S)-methyl-N-methylazetidinone, $FX_2$. Add 3-[(S)-2'-propenyl]-2-(S)-methyl-N-methylazetidinone ($FX_1$, 231 g) and H₂O (3.0 L) to a 5 L flask. Cool the solution to 0° C. then pass ozone through the solution for 8 hours. Slowly quench the ozonide intermediate with NaBH$_4$ (50 g) while maintaining the internal temperature<10° C. Bring the aqueous layer to near saturation with 1 kg NaCl, and then extract the product with CH$_2$Cl$_2$ (4×2 L). After solvent removal, the material is purified by silica gel chromatography (8% MeOH:EtOAc) to yield 160 g (69%) of 3-[(S)-2'-hydroxyethyl]-2-(S)-methyl-N-methylazetidinone. $^{13}$CNMR (CDCl$_3$, ppm δ) 17.38, 26.44, 31.63 55.56, 56.02, 61.32, 170.61.

Step 3 of CHART FX1. Synthesis of 3-[(S)-2'-methanesulfonylethyl]-2-(S)-methyl-N- methylazetidinone, FX1$_3$. Add 3-[(S)-2'-hydroxyethyl]-2-(S)-methyl-N-methylazetidinone (FX1$_2$, 100 g), THF (1.0 L), and triethylamine (920 g) to a 2 L flask. The solution is cooled to −40° C. and methanesulfonyl chloride (84.0 g) is added over 20 min maintaining the internal reaction temperature about or less than −25° C. After the white precipitate of triethylaminehydrochloride is filtered off, the solution of 3-[(S)-2'-methanesulfonylethyl]-2-(S)-methyl-N-methylazetidinone in THF is used directly in the next step, but it can be isolated as a yellow oil. $^{13}$CNMR (CDCl$_3$, ppm δ) 17.39, 26.41, 28.37, 37.48, 54.21, 55.77, 68.44, 168.89.

Steps 4 and 5 of CHART FX1. Synthesis of 3-[(S)-2'-N-benzylaminoethyl]-2-(S)-methyl-N-methylazetidinone, FX1$_4$, and 3-[1'-[(S)-methylamino]ethyl]-N-benzylpyrrolidinone, FX1$_5$. A solution of benzylamine (223 g) in THF (1.0 L) is heated to reflux. A solution of 3-[(S)-2'-methanesulfonylethyl]-2-(S)-methyl-N-methylazetidinone (FX1$_3$, 1.4 kg) is dripped into the refluxing benzylamine solution from an addition funnel over 10 min. Reflux in THF is continued for 16 h until the 3-[(S)-2'-methanesulfonylethyl]-2-(S)-methyl-N-methylazetidinone, which is initially converted to 3-[(S)-2'-N-benzylaminoethyl]-2-(S)-methyl-N-methylazetidinone, is exhausted. The 3-[(S)-2'-N-benzylaminoethyl]-2-(S)-methyl-N-methylazetidinone thermally rearranges to 3-[1'-[(S)-methylamino]ethyl]-N-benzylpyrrolidinone under the reaction conditions. Removal of the THF by distillation, replacement with toluene (2.0 L), and continued reflux completes the transformation of 3-[(S)-2'-N-benzylaminoethyl]-2-(S)-methyl-N-methylazetidinone to 3-[1'-[(S)-methylamino]ethyl]-N-benzylpyrrolidinone. After solvent removal, purification by silica gel chromatography (15% MeOH:EtOAc w/ 1% NH$_4$OH) yielded 113 g (69%) of 3-[1'-[(S)-methylamino]ethyl]-N-benzylpyrrolidinone. $^{13}$CNMR (CDCl$_3$, ppm δ) 16.21, 20.71, 33.52, 44.68, 45.31, 46.45, 56.29, 127.41, 127.94, 128.52, 136.25, 175.51. Note that 3-[(S)-2'-N-benzylaminoethyl]-2-(S)-methyl-N-methylazetidinone, FX1$_4$, was made and isolated by an alternate route. $^{13}$CNMR (CDCl$_3$, ppm δ) 17.56, 26.25, 28.95, 47.50, 54.06, 55.66, 56.32, 127.15, 128.32, 128.60, 140.37, 170.07.

Step 6 of CHART FX1. Synthesis of 3-[1'-[(S)-methylamino]ethyl]-N-benzylpyrrolidine, FX1$_6$. Add a 1.1M solution of LiAlH$_4$ (392 mL, 431 mmol) to a 2 L flask. Heat the solution to reflux and add a solution of 3-[1'-[(S)-methylamino]ethyl]-N-benzylpyrrolidinone (FX1$_5$, 100 g) in THF (100 mL) is over 10 min. After stirring for 30 min, cool the solution to −30° C. and quench slowly with 10% NaOH (183 g). A 50% citric acid solution is added until a pH of 9 is obtained. The product is extracted with EtOAc (2×1 L), and the solvent is removed in vacuo to give 70 g (75%) of 3-[1'-[(S)-methylamino]ethyl]-N-benzylpyrrolidine. $^{13}$CNMR (CDCl$_3$, ppm δ) 17.81, 27.94, 34.09, 44.04, 54.40, 58.04, 59.28, 61.01, 127.09, 128.43, 129.04, 139.45.

Step 7 of CHART FX. Synthesis of 3-[1'-[(S)-methylamino]ethyl]benzylpyrrolidine, FX1$_7$. Add 20 wt % Pd(OH)$_2$ on carbon (12.0 g) to a 3 L autoclave followed by methanol and 3-[1'-[(S)-methylamino]ethyl]-N-benzylpyrrolidine (FX$_6$, 112 g) The autoclave is pressurized to 70 atm with H$_2$ and heated to 65° C. No H$_2$ uptake after 18 hours indicates the reaction is complete. The catalyst is filtered off, and the solvent is removed in vacuo to yield 70 g (100%) of 3-[1'-[(S)-methylamino]ethyl] benzylpyrrolidine. $^{13}$CNMR (CDCl$_3$, ppm δ) 17.85, 29.37, 33.70, 45.89, 46.76, 50.34, 58.44.

CHART AG

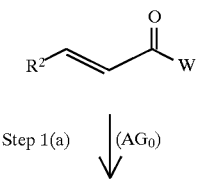

Step 1(a)   (AG$_0$)

-continued
CHART AG
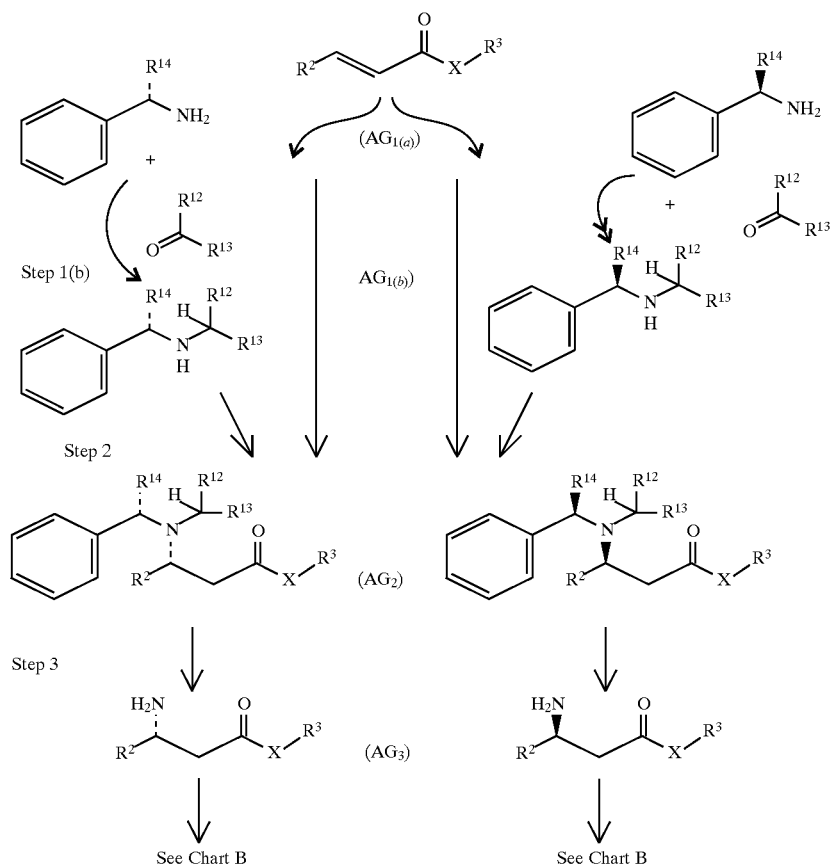
CHART AXI
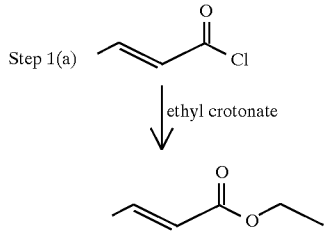
-continued
CHART AXI
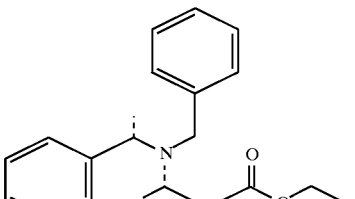
S-ethyl-3-((N-benzyl)(S-N-methylbenzyl))aminobutyrate
ethyl (S)-3-aminobutyrate
CHART BG
(AG₃ is BG₀ from CHART A)
(BG₀)
Step 1

CHART BG
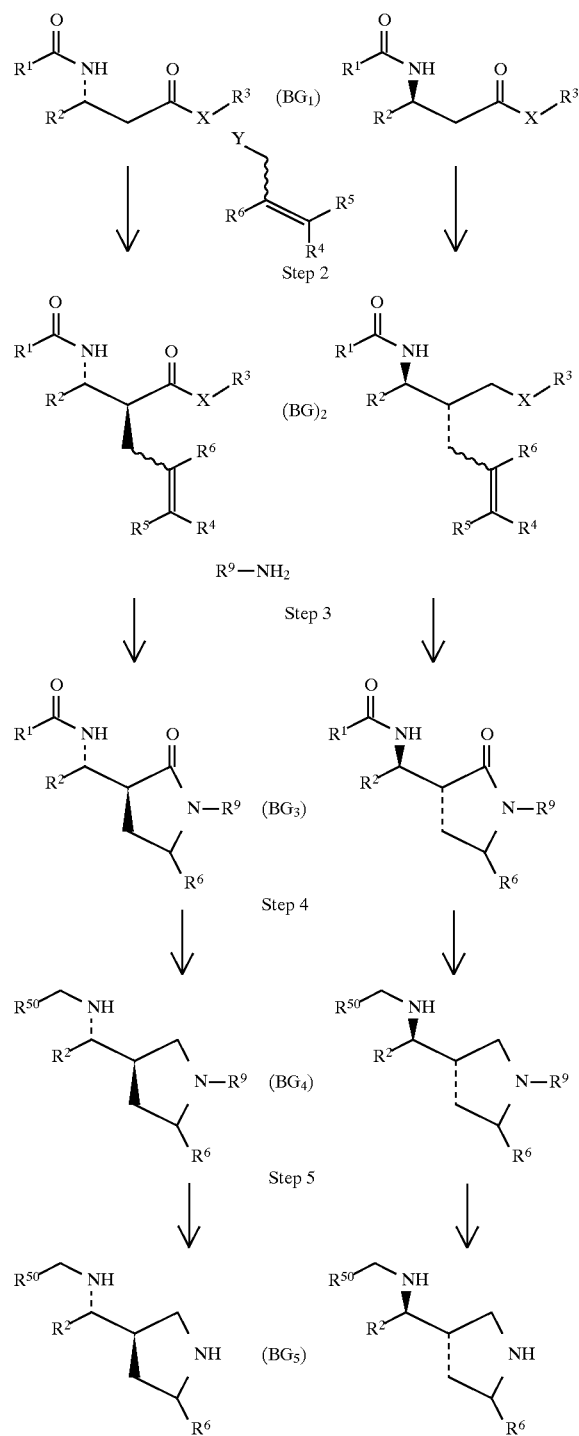
CHART BXI
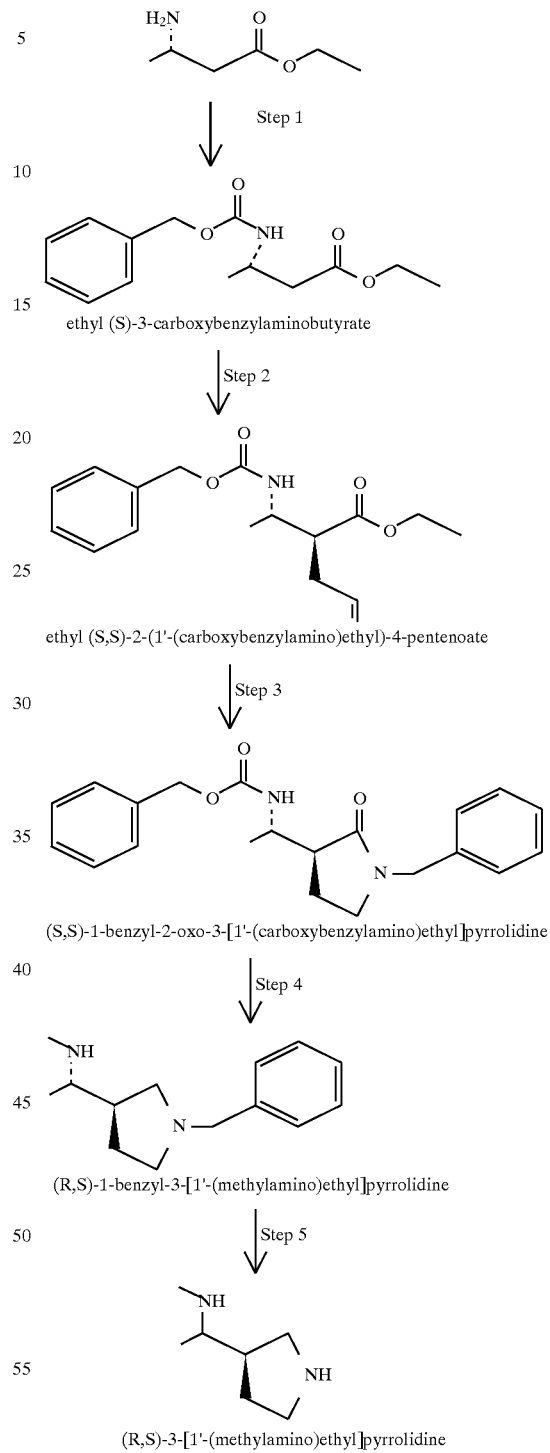

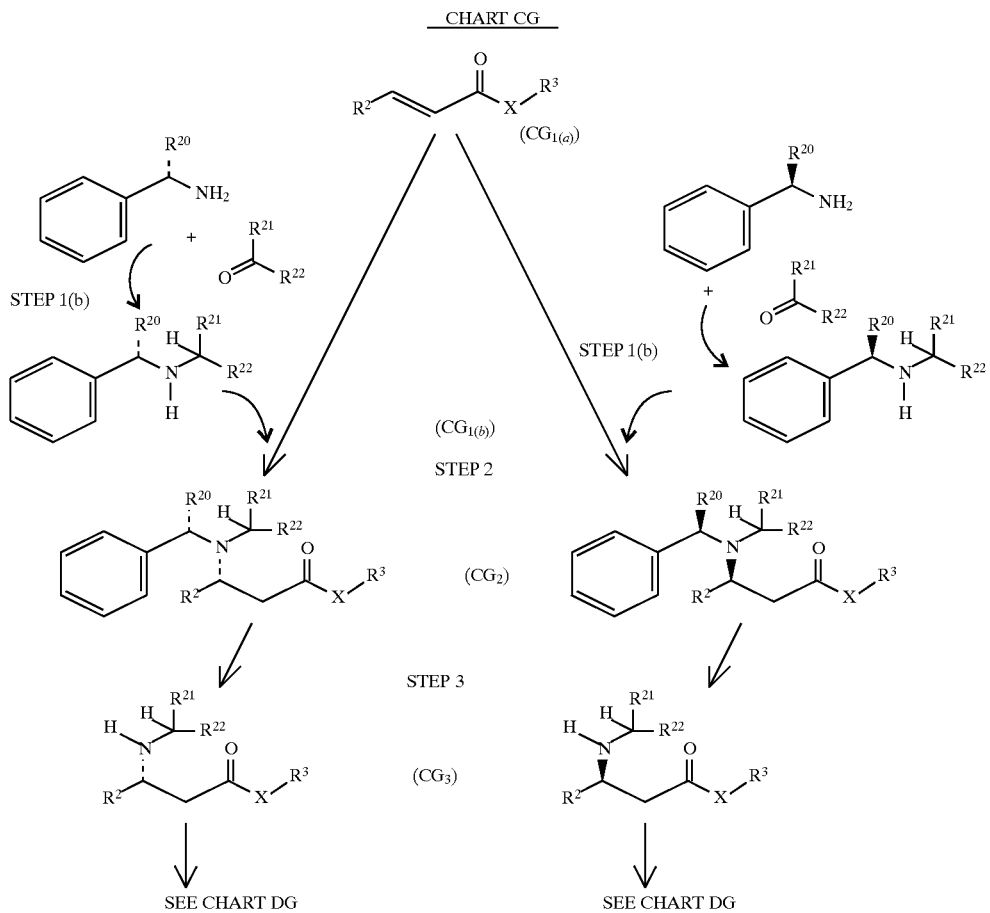
CHART CG
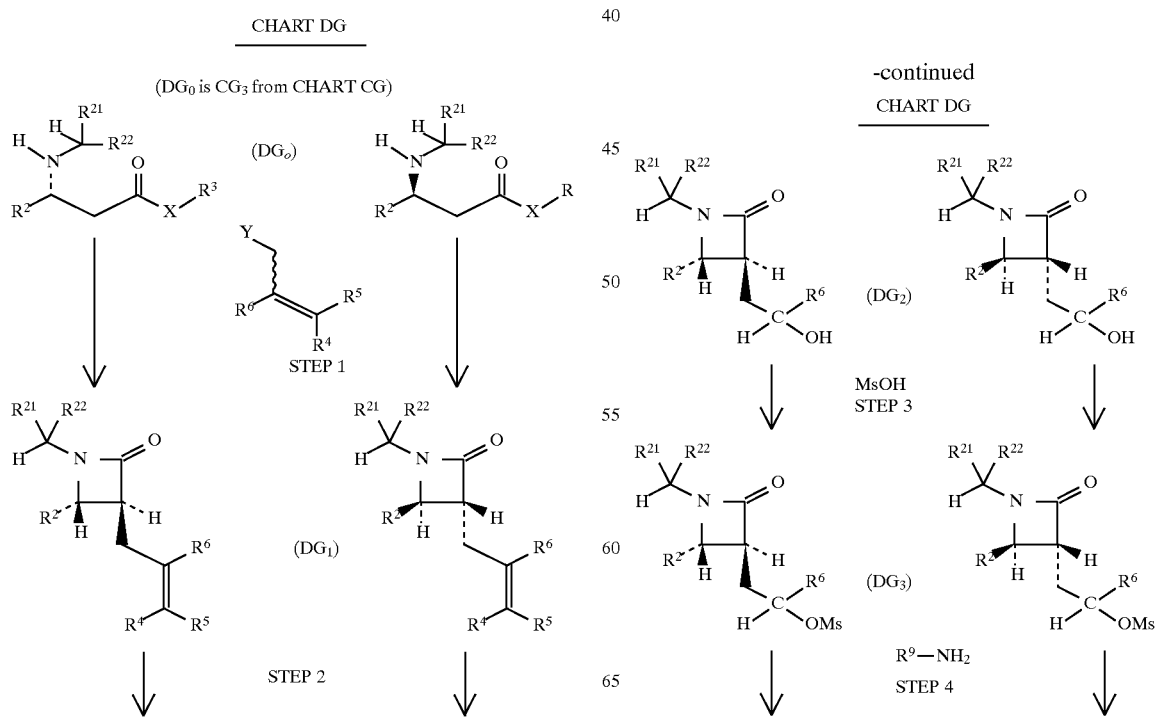
CHART DG

CHART DG
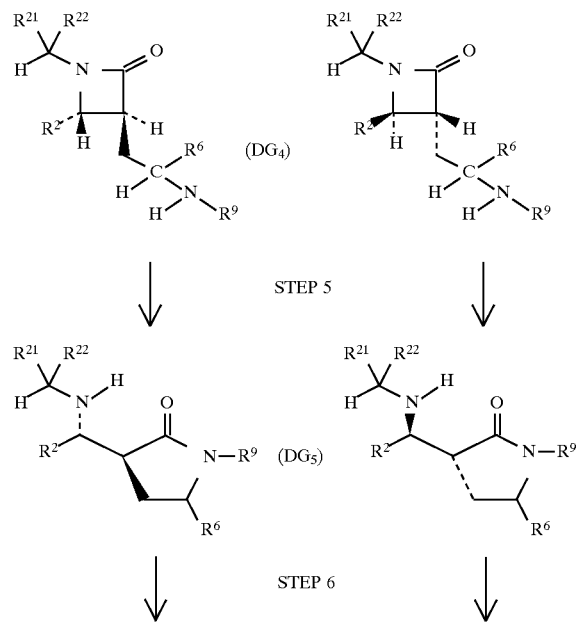
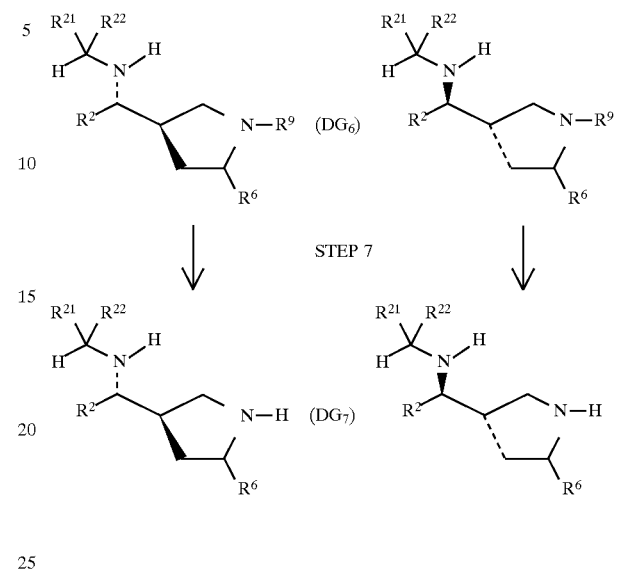
CHART EG
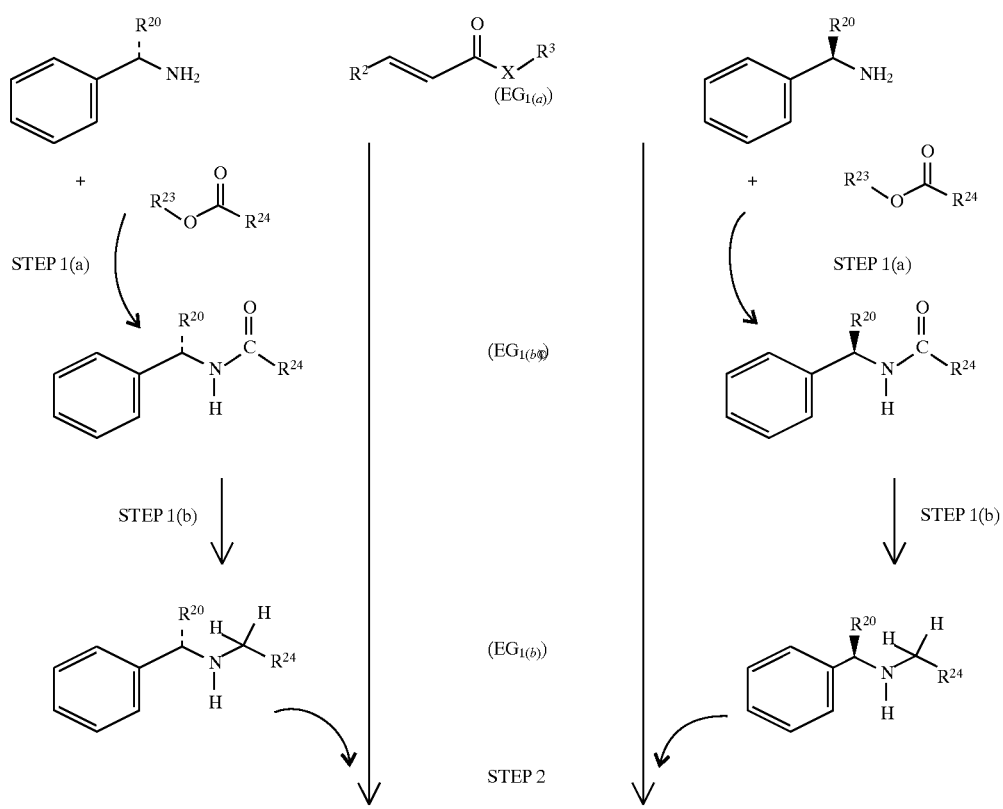

-continued
CHART EG
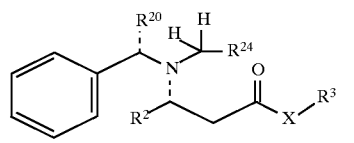
(EG2)
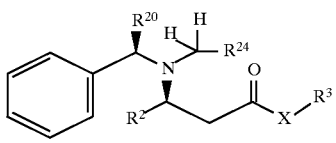
STEP 3
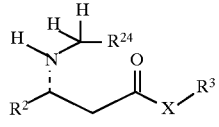
(EG3)
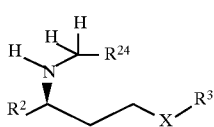
↓
↓
SEE CHART FG
SEE CHART FG
CHART EX
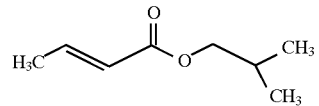
(EX1_{1(a)})
isobutyl crotonate
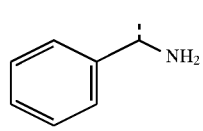
+
STEP 1(a)
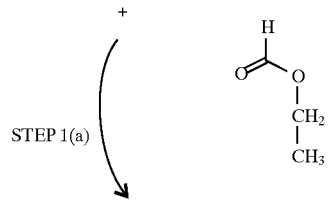
(EX1_{1(b§)})
STEP 1(b)
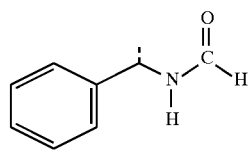
(EX1_{1(b)})
STEP 2

-continued
CHART EX
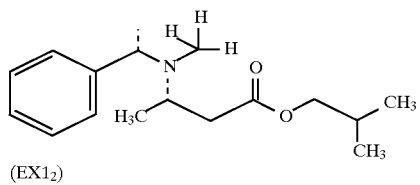
(EX1₂)
STEP 3 ↓
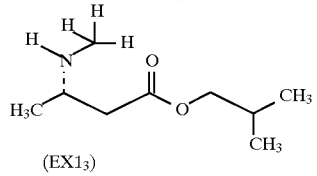
(EX1₃)
↓
SEE CHART FX1
CHART FG
(FG₀ is EG₃ from CHART EG)
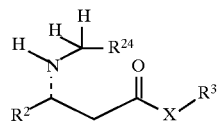  (FG₀)  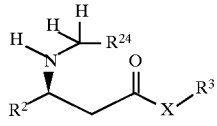
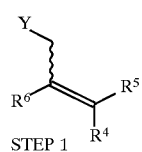
STEP 1
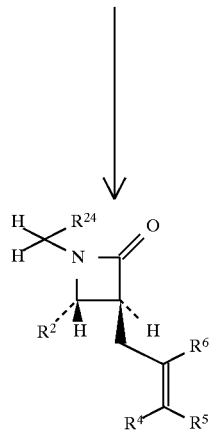  (FG₁)  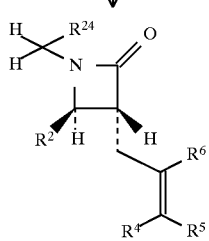
↓  STEP 2  ↓

-continued
CHART FG
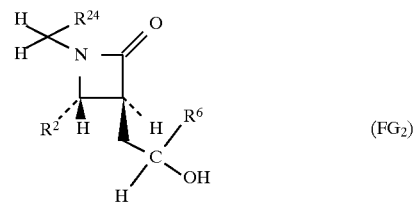 (FG$_2$)  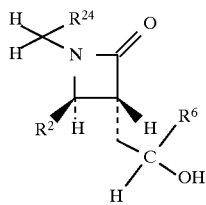
MsOH
STEP 3
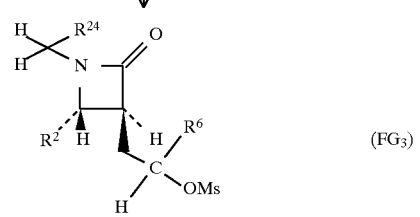 (FG$_3$)  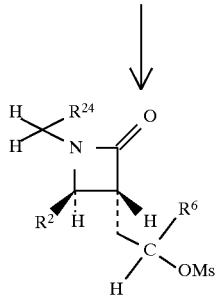
R$^9$—NH$_2$
STEP 4
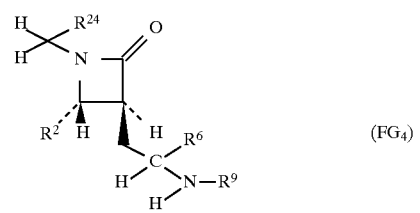 (FG$_4$)  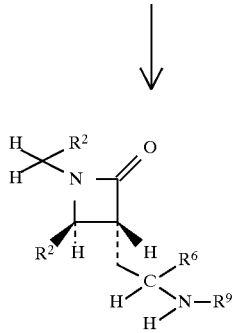
STEP 5
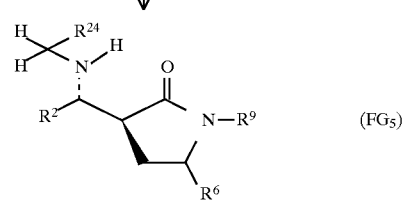 (FG$_5$)  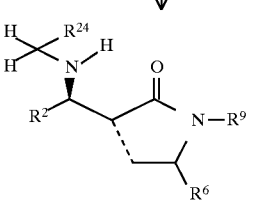
STEP 6
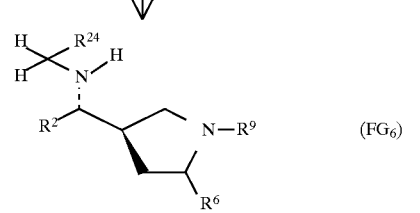 (FG$_6$)  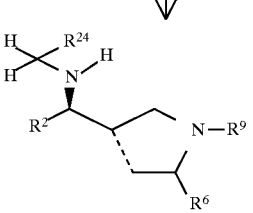
STEP 7

-continued
CHART FG
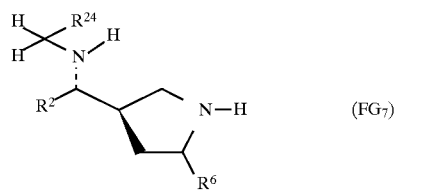
(FG₇)
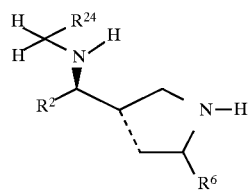
CHART FX
(FX1₀ is EX1₃ from CHART EX1)
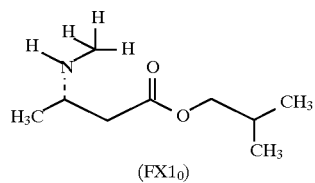
(FX1₀)
STEP 1
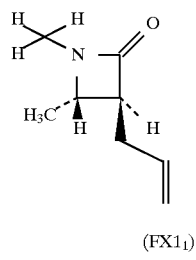
(FX1₁)
STEP 2
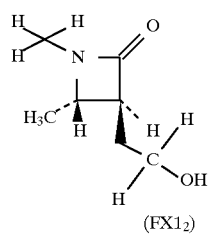
(FX1₂)
MsOH
STEP 3
-continued
CHART FX
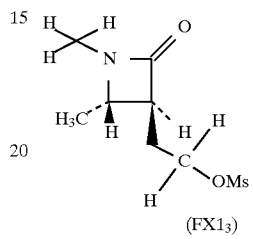
(FX1₃)
STEP 4
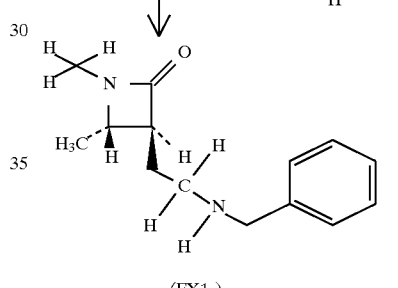
(FX1₄)
STEP 5
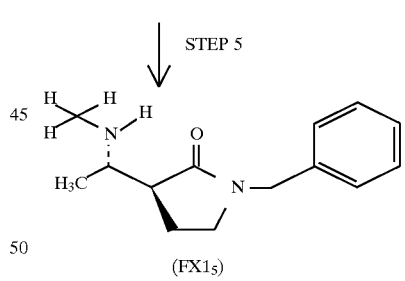
(FX1₅)
STEP 6
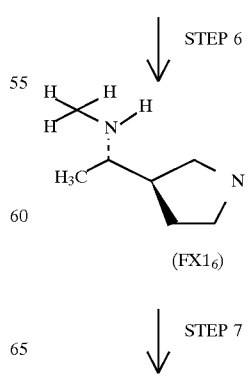
(FX1₆)
STEP 7

-continued
CHART FX

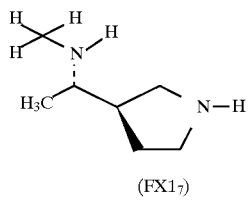

(FX1₇)

We claim:

1. The process for the preparation of a compound or the compounds represented by the structures on the left side, or the right side of FIG. $DG_1$, below, or, if the starting materials are a racemic mixture, the reaction may produce a mixed ratio of compounds represented on both sides of the FIG. $DG_1$, below,

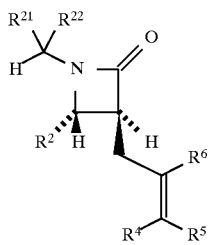

FIG. $DG_1$

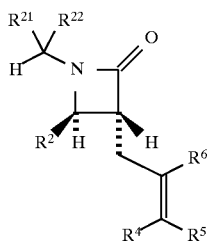

where the variables are defined below, which comprises a series of reactions, the reactions beginning with a compound represented by the structures in FIGS. $DG_0$, below,

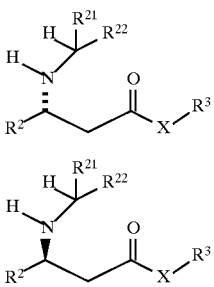

FIG. $DG_0$

where $R^2$ and $R^3$ are defined independently and are lower alkyl, alkylaryl, or optionally substituted aryl; where $R^{21}$ and $R^{22}$ are defined independently and are H, -$(C_1-C_8)$alkyl, -$(C_3-C_8)$cycloalkyl, -$(C_1-C_8)$alkyl-$(C_3-C_8)$cycloalkyl, -$(C_6-C_{12}$ aryl), -$(C_1-C_8)$alkyl-$(C_6-C_{12}$ aryl), or the aryl or alkyl is substituted with one to three of the following groups, -$(C_6-C_{12}$ aryl), -$(C_1-C_3)$alkyl, -$(C_1-C_3)$ alkoxy, halogen, trifluoromethyl; and where X is O, NH, S; are dissolved in a suitable organic solvent, and then added, in a cool temperature to control exothermic formations under an inert atmosphere, to a solution of a compound of the description in FIG. GRX, dissolved in a suitable organic solvent,

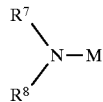

FIG. GRX where $R^7$ and $R^8$ are defined independently and are -$(C_1-C_8)$ alkyl, -$(C_3-C_8)$cycloalkyl, -$(C_1-C_8)$alkyl-M is Li, Na, or K; the resulting anion or dianion is then reacted with a compound represented by the structure shown in FIG. GYX below,

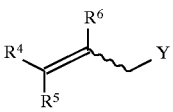

FIG. GYX where $R^4$, $R^5$, and $R^6$ are independent and are H, alkyl, alkylaryl, or optionally substituted aryl, and where Y is halogen, —OTs, —OMs, or —OTf; to obtain the desired compound or compounds.

2. The process for the preparation of a compound or the compounds represented by the structures on the left side, or the right side of FIG. $FG_1$, below, or, if the starting materials are a racemic mixture, the reaction may produce a mixed ratio of compounds represented on both sides of the FIG. $FG_1$, below,

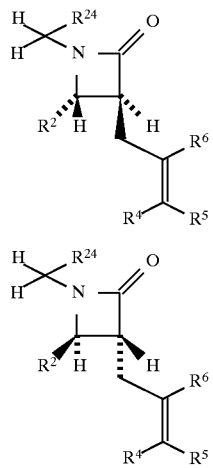

FIG. $FG_1$

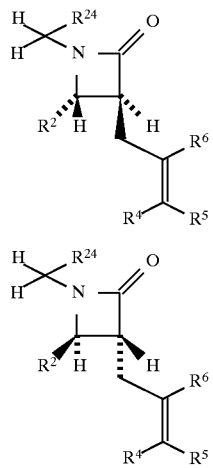

where the variables are defined below, which comprises a series of reactions, the reactions beginning with a compound represented by the structures in FIG. $FG_0$, below,

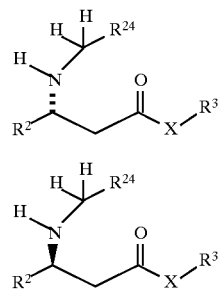

FIG. $FG_0$

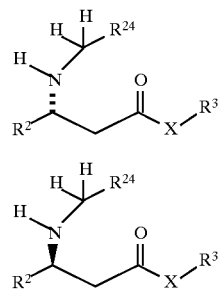

where $R^2$ and $R^3$ are defined independently and are -$(C_1-C_8)$ alkyl, -$(C_3-C_8)$cycloalkyl, -$(C_1-C_8)$alkyl-$(C_3-C_8)$ cycloalkyl, -$(C_6-C_{12}$ aryl), -$(C_1-C_8)$alkyl-$(C_6-C_{12}$ aryl), or the aryl or alkyl is substituted with one to three of the following groups, -$(C_6-C_{12}$ aryl), -$(C_1-C_3)$alkyl, -$(C_1-C_3)$ alkyl, -$C_1-C_3)$ alkoxy, halogen, trifluoromethyl; where $R^{24}$ is H, -(C$_1$–C$_8$)alkyl, -(C$_3$–C$_8$)cycloalkyl, -(C$_1$–C$_8$)alkyl-(C$_3$–C$_8$)cycloalkyl, -(C$_6$–C$_{12}$ aryl), -(C$_1$–C$_8$)alkyl-(C$_6$–C$_{12}$ aryl), or the aryl or alkyl is substituted with one to three of the following groups, -(C$_6$–C$_{12}$)aryl, -(C$_1$–C$_3$)alkyl, -(C$_1$–C$_3$)alkoxy, halogen, trifluoromethyl; and where X is O, NH, S; is dissolved in a suitable organic solvent, and added, between a temperature of –50° C. and 0° C. in a nitrogen atmosphere, to a solution of a compound represented by the structures shown in FIG. GRX, below,

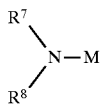

FIG. GRX where R$^7$ and R$^8$ are defined independently and are -(C$_1$–C$_8$) alkyl, -(C$_3$–C$_8$)cycloalkyl, -(C$_1$–C$_8$)alkyl-(C$_6$–C$_{12}$)aryl; and M is Li, Na, or K;

the resulting anion or dianion is then reacted with a compound represented by the structures shown in FIG. GYX, below,

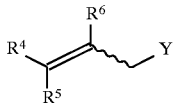

FIG. GYX where R$^4$, R$^5$ and R$^6$ are defined independently and are H, -(C$_1$–C$_8$)alkyl, -(C$_3$–C$_8$)cycloalkyl, -(C$_1$–C$_8$)alkyl-(C$_3$–C$_8$) cycloalkyl, -(C$_6$–C$_{12}$ aryl), -(C$_1$–C$_8$)alkyl-(C$_6$–C$_{12}$ aryl), or the aryl or alkyl is substituted with one to three of the following groups, (C$_6$–C$_{12}$ aryl), (C$_1$–C$_3$)alkyl, (C$_1$–C$_3$) alkoxy, halogen, trifluoromethyl, and where Y is halogen, —OTs, —OMs, or —OTf; to produce the desired compounds.

3. A compound selected from the following, compounds, represented by the following structures, shown in FIG. FG$_1$, below,

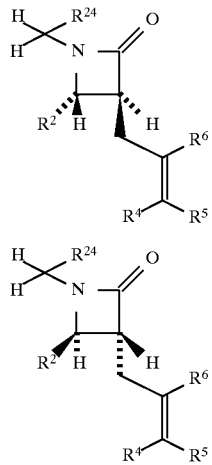

FIG. FG$_1$ or shown in FIG. FG$_2$, below,

FIG. FG$_2$

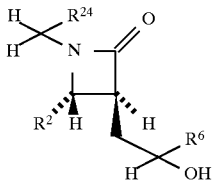

or shown in FIG. FG$_3$, below,

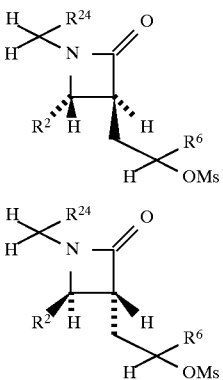

FIG. FG$_3$ where R$^2$ and R$^3$ are defined independently and are lower alkyl, alkylaryl or optionally substituted aryl; where R$^4$, R$^5$ and R$^6$ are defined independently and are H, -(C$_1$–C$_8$)alkyl, -(C$_3$–C$_8$)cycloalkyl, -(C$_1$–C$_8$)alkyl-(C$_3$–C$_8$)cycloalkyl, -(C$_6$–C$_{12}$ aryl), -(C$_1$–C$_8$)alkyl-(C$_6$–C$_{12}$ aryl), or the aryl or alkyl is substituted with one to three of the following groups, -(C$_6$–C$_{12}$ aryl), -(C$_1$–C$_3$)alkyl, -(C$_1$–C$_3$) alkoxy, halogen, trifluoromethyl;

where R$^{24}$ is H, -(C$_1$–C$_8$)alkyl, -(C$_3$–C$_8$)cycloalkyl, -(C$_1$–C$_8$)alkyl-(C$_3$–C$_8$)cycloalkyl, -(C$_6$–C$_{12}$ aryl), -(C$_1$–C$_8$) alkyl-(C$_6$–C$_{12}$ aryl), or the aryl or alkyl is substituted with one to three of the following groups, -(C$_6$–C$_{12}$)aryl, -(C$_1$–C$_3$)alkyl, -(C$_1$–C$_3$)alkoxy, halogen, trifluoromethyl;, and where Ms is mesylate.

4. A compound of claim 3 selected from the following, compounds, named or represented by the following FIGS., 3-((S)-2'-propenyl-2-(S)-methyl-N-methylazetidinone, shown in FIG. FX1$_1$, below,

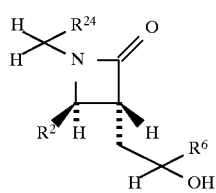

(FX1$_1$)

or the following compound, 3-((S)-2'-hydroxyethyl)-2-(S)-methyl-N-methylazetidinone, shown below in FIG. FX1$_2$, (FX1$_2$)

or the following compound, 3-((S)-2'methanesulfonylethyl)-2-(S)-methyl-N-methylazetidinone, FX1$_3$, below,

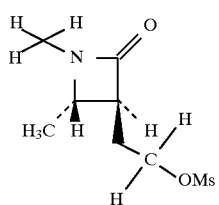

(FX1₃)

5. A compound selected from the following, compounds, represented by the following structures, shown in FIG. DG₁, below.

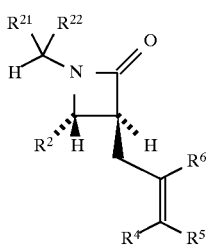

FIG. DG₁

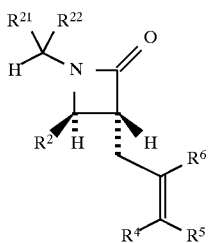

or the compounds represented by the structures shown in FIG. DG₂, below,

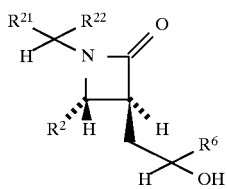

FIG. DG₂

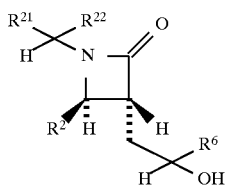

or the compounds represented by the structures shown in FIG. DG₃, below,

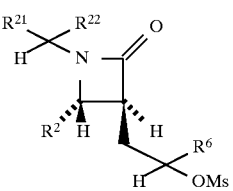

FIG. DG₃

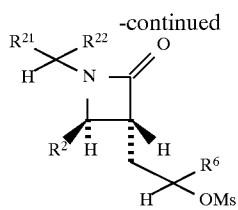
-continued where $R^2$ is -($C_1$–$C_8$)alkyl, -($C_3$–$C_8$)cycloalkyl, -($C_1$–$C_8$) alkyl-($C_3$–$C_8$)cycloalkyl, -($C_6$–$C_{12}$ aryl), -($C_1$–$C_8$)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl;

where $R^4$, $R^5$ and $R^6$ are defined independently and are H, -($C_1$–$C_8$)alkyl, -($C_3$–$C_8$)cycloalkyl, -($C_1$–$C_8$)alkyl-($C_3$–$C_8$) cycloalkyl, -($C_6$–$C_{12}$ aryl), -($C_1$–$C_8$)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl;

where $R^{21}$ and $R^{22}$ are defined independently and are H, -($C_1$–$C_8$)alkyl, -($C_3$–$C_8$)cycloalkyl, -($C_1$–$C_8$)alkyl-($C_3$–$C_8$) cycloalkyl, -($C_6$–$C_{12}$ aryl), -($C_{1-C8}$)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl; and where Ms is mesylate.

6. A compound selected from the following, compounds, represented by the following structures, shown in FIG. DG₄ below,

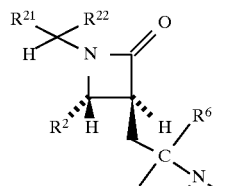

FIG DG₄

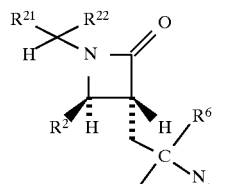

or shown in FIG. FG₄, below,

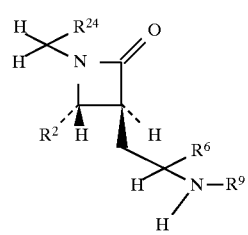

FIG. FG₄

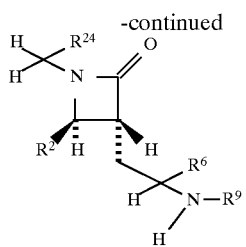

where $R^2$ is -($C_1$–$C_8$)alkyl, -($C_3$–$C_8$)cycloalkyl, -($C_1$–$C_8$) alkyl-($C_3$–$C_8$)cycloalkyl, -($C_6$–$C_{12}$ aryl), -($C_1$–$C_8$)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl; where $R^6$ is H, -($C_1$–$C_8$)alkyl, -(C3–$C_8$)cycloalkyl, -($C_1$–$C_8$)alkyl-($C_3$–$C_8$) cycloalkyl, -($C_6$–$C_{12}$ aryl), -($C_1$–$C_8$)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl;

where $R^9$ is H, -($C_1$–$C_8$)alkyl, -($C_3$–$C_8$)cycloalkyl, -($C_1$–$C_8$) alkyl-($C_3$–$C_8$)cycloalkyl, -($C_6$–C12 arl), -($C_1$–$C_8$)alkyl-($C_6$–$C_{12}$ aryl), or the aryl or alkyl is substituted with one to three of the following groups, -($C_6$–$C_{12}$ aryl), -($C_1$–$C_3$)alkyl, -$C_1$–$C_3$) alkoxy, halogen, trifluoromethyl;

where $R^{21}$, $R^{22}$, and $R^{24}$ are defined independently and are H, -($C_1$–$C_8$)alkyl, -($C_3$–$C_8$)cycloalkyl, -($C_1$–$C_8$)alkyl-($C_3$–$C_8$)cycloalkyl, -($C_6$–$C_{12}$ aryl), -($C_1$–$C_8$)alkyl-($C_6$–$C_{12}$ aryl), or the aryl or alkyl is substituted with one to three of the following groups, -($C_6$–$C_{12}$ aryl), -($C_1$–$C_3$)alkyl, -($C_1$–$C_3$) alkoxy, halogen, trifluoromethyl; and where Ms is mesylate.

* * * * *